US012751709B2

(12) United States Patent
Hiorth et al.

(10) Patent No.: US 12,751,709 B2
(45) Date of Patent: Oct. 6, 2026

(54) DEVICE FOR HEART REPAIR

(71) Applicant: CARDIOMECH AS, Trondheim (NO)

(72) Inventors: Nikolai Hiorth, Oslo (NO); Hans Emil Hiorth, Trondheim (NO)

(73) Assignee: CardioMech AS, Trondheim (NO)

( * ) Notice: Subject to any disclaimer, the term of this patent is extended or adjusted under 35 U.S.C. 154(b) by 291 days.

(21) Appl. No.: 18/037,622

(22) PCT Filed: Nov. 17, 2021

(86) PCT No.: PCT/EP2021/082045

§ 371 (c)(1),
(2) Date: May 18, 2023

(87) PCT Pub. No.: WO2022/106497

PCT Pub. Date: May 27, 2022

(65) Prior Publication Data

US 2024/0023951 A1 Jan. 25, 2024

(30) Foreign Application Priority Data

Nov. 19, 2020 (GB) ..................................... 2018203

(51) Int. Cl.
*A61B 17/04* (2006.01)
*A61F 2/24* (2006.01)

(52) U.S. Cl.
CPC ........ *A61B 17/0401* (2013.01); *A61F 2/2457* (2013.01); *A61B 2017/0409* (2013.01);
(Continued)

(58) Field of Classification Search
CPC .... A61F 2/2457; A61F 2/2463; A61F 2/2466; A61F 2/2427; A61F 2220/0016;
(Continued)

(56) References Cited

U.S. PATENT DOCUMENTS

2004/0003819 A1 1/2004 St. Goar et al.
2011/0011917 A1 1/2011 Loulmet
(Continued)

FOREIGN PATENT DOCUMENTS

WO WO 2014/195786 12/2014
WO WO 2016/042022 3/2016
(Continued)

OTHER PUBLICATIONS

International Search Report and Written Opinion issued in Corresponding PCT application No. PCT/EP2021/082045, dated Feb. 21, 2022.
(Continued)

*Primary Examiner* — Majid Jamialahmadi
(74) *Attorney, Agent, or Firm* — Norton Rose Fulbright US LLP

(57) ABSTRACT

A catheter device for repair of the heart by implanting an artificial chordae line, a method of use of a catheter device for repair of the heart by implanting an artificial chordae line, and a method of manufacture of a catheter device for repair of the heart by implanting an artificial chordae line are described. A catheter device (102) for repair of the heart by implanting an artificial chordae line (114), the catheter device (102) comprising: a housing section extending from a distal end of the catheter device along the length of the catheter device toward a proximal end of the catheter device; a leaflet anchor (110) for placement in a leaflet (12) of a heart valve, wherein the leaflet anchor (110) is arranged to be coupled to the artificial chordae line (114); and a leaflet anchor deployment mechanism for deploying the leaflet anchor (110) to attach it to the leaflet (12) of the heart, wherein the leaflet anchor deployment mechanism comprises a mechanical gripper device (106) for grasping the leaflet (12) of the heart valve, and a leaflet anchor tube (138)
(Continued)

for housing the leaflet anchor (110) in a folded configuration; the gripper device (106) and leaflet anchor (110) being arranged such that when, in use, the gripper device (106) grasps the leaflet (12), the leaflet anchor (110) can be pushed out of a leaflet anchor tube (138) to pierce the leaflet (12) and form the leaflet anchor (110) into an unfolded configuration so that hooked formations of the leaflet anchor (110) can, in use, secure the leaflet anchor (110) in the leaflet (12); wherein the mechanical gripper device (106) includes a gripper arm (130) rotatably coupled to a main body of the catheter device (102) so that the gripper arm (130) can rotate relative to the catheter device (102) to move an outer end of the gripper arm (130) away from the main body of the catheter device (102); and wherein the leaflet anchor tube (138) is arranged to implant the leaflet anchor (110) in the leaflet (12) of the heart by piercing the leaflet (12) from an atrial side of the leaflet (12).

17 Claims, 16 Drawing Sheets

(52) U.S. Cl.
CPC ................. *A61B 2017/0414* (2013.01); *A61B 2017/0438* (2013.01); *A61B 2017/0464* (2013.01)

(58) Field of Classification Search
CPC ...... A61F 2/243; A61F 2/2436; A61F 2/2439; A61F 2002/9534; A61B 17/0401; A61B 2017/0409
See application file for complete search history.

(56) References Cited

U.S. PATENT DOCUMENTS

| | | | | |
|---|---|---|---|---|
| 2014/0214152 | A1* | 7/2014 | Bielefeld | A61B 17/0487 623/2.11 |
| 2017/0252032 | A1* | 9/2017 | Hiorth | A61F 2/2457 |
| 2020/0155313 | A1* | 5/2020 | Zhang | A61B 5/06 |

FOREIGN PATENT DOCUMENTS

| | | |
|---|---|---|
| WO | WO 2017/066890 | 4/2017 |
| WO | WO 2020/109596 | 6/2020 |

OTHER PUBLICATIONS

Search Report issued in Corresponding Great Britain Application No. GB2018203.6, dated Apr. 16, 2021.

* cited by examiner

DEVICE FOR HEART REPAIR

CROSS-REFERENCE TO RELATED APPLICATIONS

This application is a national phase application under 35 U.S.C. § 371 of International Application No. PCT/EP2021/082045 filed 17 Nov. 2021, which claims priority to Great Britain Patent Application No. 2018203.6 filed 19 Nov. 2020. The entire contents of each of the above-referenced disclosures is specifically incorporated by reference herein without disclaimer.

The present invention relates to a catheter device for repair of the heart by implanting an artificial chordae line, a method of use of a catheter device for repair of the heart by implanting an artificial chordae line, and a method of manufacture of a catheter device for repair of the heart by implanting an artificial chordae line.

The chordae tendineae are cord-like tendons that connect the papillary muscles to the tricuspid valve and the mitral valve in the heart. The valves consist of leaflets that open and close with the beating of the heart in order to control blood flow and blood pressure within the heart.

Mitral valve disease presents an important challenge to cardiac surgeons and cardiologists. Mitral regurgitation has become the leading pathophysiological condition of the mitral valve in the developed world. One of the most important causes of regurgitation is prolapse of one of the mitral leaflets. The pathological abnormality that requires repair is rupture or other degenerative changes of the chords, leaflet or other related structures. When the chord(s) remain intact, the mitral leaflets open and close synchronously and in a fashion that prevents leakage of the valve. The normal chords can rupture acutely causing acute decompensation, in the form of, heart failure. This usually results in an emergency condition requiring rapid intervention. Damage to the chord(s) can also occur more slowly including rupturing or elongation due to degenerative processes, causing the mitral valve to develop leaks or regurgitation.

Surgical repair of the mitral valve has become relatively standardized, using resection of the prolapsed leaflet and/or implantation of new, artificial chordae lines to control leaflet motion. In addition a mitral ring is frequently placed to shrink the size of the mitral valve annulus. Surgical replacement of ruptured or elongated chords is highly effective in eliminating or minimizing mitral valve regurgitation. The procedure is presently performed with open heart surgery techniques. This requires use of cardiopulmonary bypass and arresting of the heart. This surgical approach, although working well, is a highly invasive procedure which can cause serious complications, long hospital stays and substantial expense. Consequently a less invasive approach would be preferable.

Insertion of mitral leaflet chords has been done using a minimally invasive surgical approach entering the heart through its apex. The technique, was developed by the company Neochord Inc. and is described, for example, in WO 2012/167120, but still requires a surgical incision and the chords do not get inserted in the papillary muscles where they normally should be fixed.

WO 2008/101113 describes another example of a system for repair of the heart, including implantation of artificial chordae lines. In the described method an anchor can be attached to the papillary muscle and is coupled to the leaflet of the mitral valve by an artificial chordae line, a suture and a clip. The clip allows for adjustment of the length of the artificial chordae line. A complex multi-stage process is required to implant the papillary anchor and the suture and join them together. The papillary anchor is formed of a memory metal such as nitinol and has a 'flowered' shape with sharp 'petals' for hooking the anchor to body tissue. The flowered shape is flattened into a tube shape and held in a tube that is passed into the heart. The tube and anchor are then pressed against the papillary muscle and the anchor is pushed out of the tube so that the petals pierce the muscle and fold outward through the muscle to provide a secure coupling of the anchor to the muscle tissue. In a subsequent surgical procedure, an artificial chordae line may be attached to the anchor. Then in a further step, the suture is attached to the leaflet and this suture is joined to the chord by the clip. The suture is attached to the leaflet by locating a vacuum port near to the leaflet and pulling it into the vacuum port where it can be pierced.

It will be appreciated that this technique, whilst avoiding open heart surgery, still requires a sequence of relatively complex steps. The number of steps required increases the risk. Furthermore, the complexity of the device means that parts implanted within the body are at risk of coming loose and injuring the patient by embolization. In particular, the clip could come loose from the anchors. It is also thought that the use of a suture with an additional clip, as proposed, may not effectively repair the heart valve since it will not closely simulate a natural chord.

In earlier patent applications, WO2016/042022 and WO2020/109596, the present applicant disclosed catheter devices for implanting an artificial chordae line to repair a heart valve. The catheter devices of WO2016/042022 and WO2020/109596 include a mechanical gripper device for grasping the leaflet of the heart valve, with a leaflet anchor housed in the gripper. The leaflet anchor can be formed from a flexible material, such as nitinol, with a grapple hook shape in an unfolded configuration, and being able to deform elastically into the folded configuration, for example when constrained within a leaflet anchor channel in the gripper device. The hooks are straightened out when the leaflet anchor is in the folded configuration. When the leaflet is grasped by the gripper device then the leaflet anchor can be pushed out of the gripper to drive the hooks though the leaflet whilst they return elastically to the unfolded configuration, thereby securing the leaflet anchor in the leaflet. In each of WO2016/042022 and WO2020/109596, the disclosed embodiments generally require that the gripper arm contact the leaflet of the heart valve from a ventricular side. The leaflet anchor, deployed from the leaflet anchor channel in the gripper device, is therefore implanted into the leaflet from the ventricular side.

The devices described in WO2016/042022 and WO2020/109596 also use a papillary anchor with a broadly similar arrangement of foldable hooks. The papillary anchor is held within a tube of the catheter device in a folded configuration and can be pushed out of the tube with the hooks being driven through the papillary muscle whilst they return elastically to the unfolded configuration, thereby securing the papillary anchor to the muscle. The papillary anchor includes a locking ring acting as a locking mechanism for clamping an artificial chordae line when no force is applied. The locking ring maybe elastically deformed to release the line from the locking mechanism for adjustment of the length of the chordae line.

Whilst the devices of WO2016/042022 and WO2020/109596 provided significant advances in this field it has been found that further refinement of the design may be advantageous. The present disclosure relates to new features building on the design of the devices disclosed in WO2016/042022 and WO 2020/109596 in various respects.

It is therefore an objective of the discussed embodiments to provide an improved catheter device for repair of the heart by implanting an artificial chordae line.

Viewed from a first aspect of the present invention, there is provided a catheter device for repair of the heart by implanting an artificial chordae line, the catheter device comprising: a housing section extending from a distal end of the catheter device along the length of the catheter device toward a proximal end of the catheter device; a leaflet anchor for placement in a leaflet of a heart valve, wherein the leaflet anchor is arranged to be coupled to the artificial chordae line; and a leaflet anchor deployment mechanism for deploying the leaflet anchor to attach it to the leaflet of the heart, wherein the leaflet anchor deployment mechanism comprises a mechanical gripper device for grasping the leaflet of the heart valve, and a leaflet anchor tube for housing the leaflet anchor in a folded configuration; the gripper device and leaflet anchor being arranged such that when, in use, the gripper device grasps the leaflet, the leaflet anchor can be pushed out of a leaflet anchor tube to pierce the leaflet and form the leaflet anchor into an unfolded configuration so that hooked formations of the leaflet anchor can, in use, secure the leaflet anchor in the leaflet; wherein the mechanical gripper device includes a gripper arm rotatably coupled to a main body of the catheter device so that the gripper arm can rotate relative to the catheter device to move an outer end of the gripper arm away from the main body of the catheter device; and wherein the leaflet anchor tube is arranged to implant the leaflet anchor in the leaflet of the heart by piercing the leaflet from an atrial side of the leaflet.

This device allows a leaflet to be easily gripped and a new chord securely attached to the leaflet. There is no need for a complex procedure involving the use of vacuum and sutures as in WO 2008/101113. The mechanical gripper device can be opened and closed several times if required to release and re-engage the leaflet until it is in the desired position for the anchor to be placed. The piercing of the leaflet involves a single movement of the leaflet anchor, in contrast to the device of WO 2008/101113, where it is required to first pierce with a needle passing in one direction, and then pull through a suture in the other direction. Thus the device of the first aspect is simpler and more effective than the prior art device.

The previous catheter devices of WO2016/042022 and WO2020/109596 generally contemplated the implantation of the leaflet anchor in the leaflet of the heart by piercing the leaflet from a ventricular side of the leaflet, rather than an atrial side of the leaflet. However, the present applicant recognises that a catheter device which implants a leaflet anchor from an atrial side of the leaflet provides a number of advantages which may not be present when a leaflet anchor is implanted from a ventricular side of the leaflet of the heart.

When implanted from a ventricular side of the leaflet, the leaflet anchor may need to be located towards an edge of the leaflet in order to provide adequate support to the flailing leaflet. In contrast, when implanted from an atrial side of the leaflet, the leaflet anchor may provide adequate support to the edge of the leaflet when the leaflet anchor is implanted towards the edge of the leaflet, or towards an annulus of the leaflet.

The chosen location of implantation of the leaflet anchor may depend on a number of factors, and may be patient-specific. Implanting the leaflet anchor in an atrial side of the leaflet may provide a surgeon with greater flexibility in choosing where to implant the leaflet anchor, i.e. by being able to implant the leaflet anchor towards an edge of the leaflet, towards an annulus of the leaflet, or in between.

The tissue of the leaflet closer to the annulus, rather than towards an edge of the leaflet, may be less prone to experiencing trauma associated with the implantation of the leaflet anchor. The tissue towards the annulus of the leaflet may be thicker than that closer to the leaflet edge, for example. The tissue towards the annulus of the leaflet may be more able to withstand the tension associated with the artificial chordae line during the cardiac cycle, when the line is taut.

By implanting the leaflet anchor from the atrial side, the leaflet anchor may be able to be implanted closer towards an annulus of the leaflet of the heart whilst still providing adequate support to the edge of the leaflet.

When the artificial chordae line is used to prevent mitral regurgitation the line will generally be fixed at two ends, with one end located at/in the papillary muscle of the heart, and the other located at the leaflet anchor. If the leaflet anchor is therefore implanted in the leaflet from the ventricular side, the line will extend to the papillary muscle without providing any support to the edge of the leaflet, i.e. at a flailing end of the leaflet. However, when implanted in the leaflet from the atrial side, the line may extend along an atrial-side surface of the leaflet, and extend over the edge of the leaflet before descending into the ventricle to the location of implantation in the papillary muscle. As such, the line may provide support to the flailing edge of the leaflet with the anchor implanted towards the leaflet annulus. This may also better replicate the action of chordae tendineae located towards the edge of the leaflet of the heart valve.

The leaflet anchor may be arranged to be deployed such that the artificial chordae line will be in contact with an atrial side of the leaflet of the heart between the leaflet anchor and an edge of the leaflet of the heart valve.

When the leaflet anchor is implanted from the atrial side, it will be understood that the artificial chordae line may provide support to the flailing edge when implanted in the atrial side of the leaflet, given that the line will descend from the atrial side to the ventricular side through the mitral valve over an edge of the leaflet, when the line is implanted. This may be particularly beneficial when treating flailing leaflets.

The previous catheter devices of WO2016/042022 and WO2020/109596 may generally require precise implantation of the leaflet anchor in the leaflet to provide adequate support to the edge of the leaflet. As the leaflet anchor does not provide any additional support to the edge of the leaflet other than its own implantation, the location of implantation of the anchor determines how much support is provided to the edge of the leaflet. Accordingly, implantation of the leaflet anchor may need to be more precise to ensure adequate support to the edge of the leaflet.

However, due to the contact of the artificial chordae line with the edge of the leaflet when the leaflet anchor is implanted in the atrial side of the leaflet, the location of implantation of the leaflet anchor of the present invention need not be so precise, as additional support is provided to the edge of the leaflet regardless of whether the leaflet anchor is implanted towards the edge of the leaflet or towards the atrial annulus of the leaflet. This may result in more efficient implantation of the leaflet anchor, as movement of the leaflet during the cardiac cycle which may alter the location of implantation of the leaflet anchor will be of lesser detriment to the overall support provided by the leaflet anchor.

The artificial chordae line may have a varying cross-sectional area. The artificial chordae line may have a first cross-sectional area at an end distal to the leaflet anchor and/or configured to be located at/in the papillary muscle. The artificial chordae line may have a second cross-sectional area at an end proximal to and/or attached to the leaflet anchor.

The first cross-sectional area and the second cross-sectional area may be different. The second cross-sectional area may be a rectangular cross-sectional area. The second cross-sectional area may be an oval cross-sectional area. A major axis of the second cross-sectional area may be configured to be parallel to an atrial surface of the leaflet anchor. The second cross-sectional area may be greater than the first cross-sectional area. The first cross-sectional area may be circular.

By providing an artificial chordae line comprising a second cross-sectional area as discussed, the surface are of the artificial line which is in contact with the atrial side of the leaflet may be increased. The artificial chordae line may therefore provide a greater degree of support to the flailing leaflet when implanted.

The artificial chordae line may comprise a plurality of sutures. The plurality of sutures may increase an area of contact between the artificial chordae line and the atrial side of the leaflet, such that a greater degree of support is provided to the flailing leaflet by the artificial chordae line. Additionally, if one of the plurality of sutures fails, there is a redundancy introduced such that one or more of the plurality of sutures may still be successfully implanted.

The catheter device comprises a housing section extending from a distal end towards a proximal end of the catheter device. The most distal end of the catheter device may be where the artificial chordae line is generally implanted from, whilst the proximal end may be located at an opposite end of the catheter device. The catheter device may generally be inserted into the body in a direction aligned with the direction of extension from the proximal end to the distal end of the catheter device.

The leaflet anchor tube may take the form of a generally cylindrical channel sized to be slightly larger than the leaflet anchor in its folded configuration.

The leaflet anchor may be formed from an elastic material and to be arranged so that it assumes the unfolded configuration when no force is applied, and to be able to deform elastically into the folded configuration, for example when constrained within the leaflet anchor tube.

The leaflet anchor may be arranged to be deployed by pushing it out of an opening at the end of the leaflet anchor tube, wherein the opening is arranged to be in contact with an atrial side of the leaflet of the heart during deployment.

Placing the opening of the leaflet anchor tube in contact with the atrial side of the leaflet of the heart during deployment may facilitate the implantation of the leaflet anchor from the atrial side of the leaflet. For example, placing the opening in contact with the atrial side may ensure proper placement, location and deployment of the anchor as it assumes its unfolded configuration from its elastically folded configuration.

The leaflet anchor may be arranged to be pushed out of the leaflet anchor deployment mechanism from the proximal end of the catheter device toward the distal end of the catheter device.

The catheter device may comprise a linear-shaped rod for deployment of the leaflet anchor. The linear-shaped rod may be configured to push the leaflet anchor out of the leaflet anchor deployment mechanism.

The previous devices disclosed in WO2016/042022 and WO2020/109596 each taught a U-shaped rod for pushing the leaflet anchor out of the leaflet anchor deployment mechanism. The U-shaped rod was required in each of these prior art devices due to the leaflet anchor being deployed in a ventricular side of the leaflet, i.e. beneath the leaflet. However, for the present device, the leaflet anchor is configured to be implanted in an atrial side of the leaflet. Accordingly the leaflet is approached from above, and as such the leaflet anchor is deployed in a distal direction of the catheter device. In other words, the leaflet anchor is deployed in the same direction by which the catheter device approaches the leaflet of the heart.

As such, a linear rod may be used. The linear rod, being linear, may generally be easier to manufacture. The linear rod may also be easier to arrange in the catheter device, along any other number of wires, rods and the like for operating other components located in the distal end of the catheter device. As such the linear rod may ease manufacture of the catheter device, particularly when compared to previous U-shaped rod designs.

The catheter device may generally approach the location of implantation from an atrial side of the heart rather than a ventricular side of the heart due to known techniques of insertion of the catheter device into the heart. That is, on approach a distal end of the catheter device will be oriented towards the atrial side of the leaflet of the heart. As such, to facilitate deployment of the leaflet anchor in the atrial side of the leaflet (the surface of which will be oriented towards the proximal end of the catheter device), the leaflet anchor may be pushed out of the leaflet anchor deployment mechanism from the proximal end of the catheter device toward the distal end of the catheter device.

The leaflet anchor tube may be formed in the main body of the catheter device. The leaflet anchor tube may not be formed in the gripper device. An opening of the leaflet anchor tube may be located on a surface of the main body of the catheter device, such that the leaflet anchor may be deployed from the main body of the catheter device. The opening may be located such that the leaflet anchor is deployed from a circumferential surface and/or side of the catheter device.

The leaflet anchor tube may extend generally along a length of the main body of the catheter device. The leaflet anchor tube may also have a component of extension along a radius of the catheter device such that the leaflet anchor may be deployed from the catheter device from a position on the circumferential surface of the catheter device.

The present applicants have realised that forming the leaflet anchor tube in the main body of the catheter device, rather than in the gripper device, may provide a number of advantages not previously known. Thus whilst the following features are described in combination with the first aspect of the present invention, it will be understood that they may be novel and inventive in their own right.

In WO2020/109596 and WO2016/042022, a catheter device comprising a gripper arm, with the leaflet anchor tube formed in the gripper arm of the device, is contemplated. To be able to house the leaflet anchor tube within the gripper arm, the gripper arm is hence longer than the leaflet anchor in the prior art device. The extended length of the gripper arm to accommodate the leaflet anchor, and the location of deployment from the gripper arm, may effectively reduce the range of depth at which the leaflet anchor may be implanted in the leaflet.

When the leaflet anchor tube is formed in the main body of the catheter device, the gripper arm may be shorter in length than the leaflet anchor when in the folded configuration. This is possible as the leaflet anchor is not housed within the gripper arm. A shorter gripper arm may be able to grab the leaflet harder than a longer gripper arm when the same force is applied to the gripper arm. When the leaflet anchor is deployed in the leaflet at a location adjacent to a generally distal end of the gripper arm, the moment of the force associated with deploying the anchor may be reduced when using the shorter gripper arm. Thus the leaflet may be more firmly held in place during implantation of the anchor.

Additionally or alternatively, the length of the leaflet anchor may not be constrained by the length of the gripper arm. As such, when the leaflet anchor tube is formed in the main body of the catheter device, leaflet anchors longer than the length of the gripper arm may be utilised. Longer leaflet anchors may be capable of securing and/or supporting a larger portion of the leaflet of the heart, when implanted, compared to a shorter anchor.

The gripper arm may be arranged to meet an opening of the leaflet anchor tube. The leaflet anchor tube may be formed in the main body such that a surface of the gripper arm meets the opening of the leaflet anchor tube when it is held against the main body of the catheter. The opening of the leaflet anchor tube may meet a distal end of the gripper arm. The opening of the leaflet anchor tube may meet a surface of the gripper arm located towards the distal end of the gripper arm.

By arranging the gripper arm to meet an opening of the leaflet anchor tube, the leaflet anchor may be more reliably deployed at the desired location in the heart. For example, when the gripper arm grasps the leaflet, the leaflet may be held between the gripper arm and the leaflet anchor tube such that the leaflet anchor may be deployed into the leaflet at the grasped location. The gripper arm, located against a proximal side of the leaflet, may provide resistance against the leaflet as the anchor is deployed, such that the leaflet is suitably constrained during deployment.

Alternatively, the leaflet anchor tube may be housed within the gripper arm. An opening of the leaflet anchor tube may be at the end of the gripper arm and oriented towards a distal end of the catheter.

In this arrangement, it will be understood that the gripper arm may be hinged towards a proximal end of the catheter device, with a distal end of the gripper arm oriented towards a distal end of the catheter device. Thus, contrary to the gripper arms disclosed in WO2016/042022 and WO2020/109596, the gripper arm may be oriented such that the leaflet anchor is configured to be deployed in a distal direction of the catheter, rather than a proximal direction.

The opening of the leaflet anchor tube, located in the gripper arm, may be configured to meet a complementary surface of the main body of the catheter device. As such, when the leaflet is grasped by the gripper arm, the main body of the catheter device may provide resistance against the leaflet as the anchor is deployed, such that the leaflet is suitable constrained during deployment.

The gripper arm may be configured to grasp the leaflet such that the leaflet anchor tube is arranged to implant the leaflet anchor toward an annulus of the leaflet. The gripper arm may be configured in this way when the leaflet anchor tube is formed in the main body of the catheter device or the gripper arm.

For example, the gripper arm may grasp the leaflet such that an opening of the leaflet anchor tube is located towards the annulus of the leaflet. When the leaflet anchor tube is located in the main body of the catheter device, the gripper arm may grasp the leaflet from a ventricular side such that the distal end of the gripper arm is in contact with the leaflet at or towards a ventricular annulus of the leaflet, and the opening of the leaflet anchor tube is located at or towards the annulus of the leaflet on the atrial side. When the leaflet anchor tube is located in the gripper arm, the gripper arm may grasp the leaflet from an atrial side such that the distal end of the gripper arm is in contact with the leaflet at or towards the atrial annulus of the leaflet, and the opening of the leaflet anchor tube is hence located at or towards the atrial annulus of the leaflet.

The gripper arm may be additionally or alternatively configured to grasp the leaflet such that the leaflet anchor tube is arranged to implant the leaflet anchor toward an edge of the leaflet. The gripper arm may be configured in this way when the leaflet anchor tube is formed in the main body of the catheter device or the gripper arm.

The catheter device may comprise a hinge mechanism for the gripper arm, wherein the hinge mechanism is formed integrally with the material of the main body and rotates away from the main body by elastic deformation of that material.

A single wire may be provided to actuate the gripper arm by bending the hinge mechanism to rotate the end of the gripper arm away from the main body, with the gripper arm returning elastically to its rest position if no force is applied to the wire.

The gripper arm may be actuated with a single wire or with multiple wires. Advantages can be obtained if a hinge mechanism for the gripper arm is formed integrally with the material of the main body and rotates away from the main body by elastic deformation of that material. The gripper arm as well as the hinge mechanism may be formed integrally with the material of the main body. Alternatively, the gripper arm may include a separately formed arm section, such as a milled piece or a laser cut piece, with the separate arm section being attached to a hinge mechanism of the main body, for example by gluing or welding.

In some examples, the main body of the catheter device may be formed from an elastic metal such as nitinol with a hinge being provided by an elastic joint formed in the elastic metal. In that case a single wire can be used to elastically deform the gripper arm by bending an elastic joint with the main body to rotate the end of the gripper arm away from the main body, with the gripper arm returning elastically to its at rest position once no force is applied to the wire. An advantage of this is that the elastic force of the gripper arm can hold it in place against the main body of the catheter device when the force is released from the wire, without the need for a separate wire to be pulled to keep the grip on the leaflet secure. A second wire may however be implemented as a backup if it may be needed.

In other examples, the main body of the catheter device may be formed from a composite material, such as carbon or glass reinforced PEEK. The gripper arm may then be joined to the main body of the catheter device using a pin joint, the pin forming the axis of rotation of the gripper arm. The pin joint mentioned herein may be a revolute joint or a hinge joint, i.e. comprising intermeshing features with a pin or cylindrical member joining said members, the pin forming the axis of rotation for the joint.

Alternatively or in addition the gripper arm can be heat set in a "more than closed" configuration. This would allow the gripper arm to grasp tissue towards the main body of the device.

To form the gripper arm and the hinge integrally with the main body of the catheter device, the main body of the catheter may comprise an outer tube, with the gripper arm being formed as an articulated section of the outer tube. Several forms of slits and/or patterns can be formed in the tubing in order to provide a weakened hinge section allowing for bending without plastic deformation of the gripper arm.

In alternative arrangements a hinged gripper arm may be used. In that case the gripper arm may be milled, actuation in that case could be done with a spring for closing, and wire for opening, or vice versa, or with two wires (one for opening and one for closing). A pulley cut in the device can be used to redirect the pulling force from the pull wire.

The gripping surface of the gripper arm may be arranged to hold the leaflet with friction. For example the gripping surface may use a material with a high coefficient of friction and/or the gripping surface may have a texture or surface profile for increasing friction, such as a ridged or saw-toothed profile.

The housing section may be a two-part housing section. The catheter device may comprise: the two-part housing section extending from the distal end of the catheter device along the length of the catheter device toward the proximal end of the catheter device, the two-part housing section comprising a distal part at the distal end of the catheter device and a proximal part located on the proximal side of the distal part; the leaflet anchor deployment mechanism being at the proximal part of the housing section; a papillary anchor deployment mechanism at the distal part of the housing section for deployment of a papillary anchor for attachment to the papillary muscle, wherein the papillary anchor deployment mechanism is arranged for deployment of the papillary anchor by moving it outward in the distal direction relative to the distal part; and a flexible joint located between the proximal part and the distal part of the two-part housing section, wherein the flexible joint allows a centreline of the distal part to be angled relative to a centreline of the proximal part.

The two-part housing section may be arranged to be coincidentally placed between the papillary muscle and a leaflet of the heart during use of the catheter device.

The gripper arm may be provided in the proximal part of the two-part housing section and may be rotatably coupled to the catheter device. The gripper arm may be rotatably coupled via any of the above-discussed mechanisms.

The two-part housing section may be formed from two tubular sections in any suitable material, i.e. a medically appropriate material. Stainless steel or nitinol may be used. In the alternative, composite materials such as carbon-fibre or glass-fibre reinforced PEEK may be used. The catheter device may be formed via a combination of such materials with the materials for different parts of the device being selected dependent on the required characteristics of those parts. A material that allows Ultrasound to pass through and at the same time have sufficient strength is preferred, Carbon reinforced PEEK meets these demands well, and would also allow Injection moulding of the components which lowers manufacturing cost. Fibre reinforced plastic are normally not visible on X-ray, so strategically placed radiopaque markers in all components may be used to determine device component(s) position and orientation on X-ray relative to each other, as complementary information to ultrasound imaging.

The flexible joint may include a hinge element, for example with the distal part of the two-part housing section coupled to the proximal part via a pivoting mechanism or via an elastically deformable element. For example, the two parts of the housing section may be composite or metal parts coupled together by the hinge element.

The papillary anchor may be housed within the distal part of the housing section before its deployment. The papillary anchor may have a similar cross-section as the distal part of the housing section. For example, both may have a tubular form when the anchor is held in the distal part. As noted above the anchor may have a folded and an unfolded configuration allowing pins of the anchor to form into hooks within the body tissue during deployment of the papillary anchor. The papillary anchor deployment mechanism may take a similar form to that of WO2016/042022 or WO2020/109596.

In one example the papillary anchor deployment mechanism includes a first wire or rod for pushing the papillary anchor in the distal direction relative to the distal part of the two-part housing section. There may additionally be a second wire or rod for releasing the papillary anchor from the papillary anchor deployment mechanism in order to disengage the papillary anchor from the catheter device after it is implanted in the body tissue, i.e. the tissue of the papillary muscle and/or tissue adjacent to the papillary muscle.

The papillary anchor may have a chordae line attached to it, and may include a locking mechanism, such as a locking ring as in WO2016/042022 or in WO2020/109596, the locking mechanism being for clamping the chordae line when no force is applied to the locking mechanism. The locking ring may be able to be elastically deformed to release the line from the locking mechanism for adjustment of the length of the chordae line. The papillary anchor deployment mechanism may include a locking ring holder for holding the locking ring in its elastically deformed position, with the papillary anchor deployment mechanism being arranged to selectively withdraw the locking ring holder from the locking ring so that the chordae line can be locked in place after deployment of the papillary anchor and after any required adjustment of the length of the chordae line.

The leaflet anchor deployment mechanism may allow for retraction and repositioning of the leaflet anchor after deployment of the anchor into the leaflet via an ejector unit having a grasping device with a first configuration arranged to permit deployment of the leaflet anchor into the leaflet without disengagement of the leaflet anchor from the ejector unit, and a second configuration in which the leaflet anchor is reversibly released from the ejector unit; wherein in the first configuration the grasping device of the ejector unit grasps a proximal end of the leaflet anchor, whilst a distal end of the leaflet anchor is unimpeded by the grasping device to enable it to be implanted in the leaflet; and wherein in the second configuration the grasping device of the ejector unit is disengaged from the leaflet anchor.

The leaflet anchor may be retracted with a retraction tube/catheter, by pulling the chordae so the leaflet anchor folds inside the retraction tube. The retraction tube may be placed on top of a chordae only attached to the leaflet (with device removed) or a leaflet anchor placed in a poor location (partly engaged, free floating, entangled etc.). The retraction tube may be a deflectable shaft, with or without a flexible section on the tip (that allows the tip to find the leaflet anchor base, to allow retraction). Alternatively the retraction shaft may be a flexible tube that is arranged to engage with the base of the leaflet anchor. In either configuration a marker band in the tip is needed to confirm that the retraction tube is at the base of the leaflet anchor, prior to applying tension to the chordae, to prevent any unwanted damage to the implant or native tissue.

Another alternative to retract the leaflet anchor when it is free floating (not attached to anything) is to tension the chordae until the leaflet anchor can be folded inside the papillary anchor housing, either in the distal end or through an opening in the papillary anchor housing wall.

The leaflet anchor deployment mechanism include a leaflet anchor and/or a leaflet anchor deployment mechanism such as those disclosed in WO2016/042022 and WO2020/109596.

Viewed from a second aspect of the present invention, there is provided a method of use of the catheter device of the first aspect for repair of the heart by implanting an artificial chordae line, the method comprising: moving an outer end of the gripper arm away from the main body of the catheter device; grasping the leaflet between the gripper arm and the main body of the catheter device by moving the outer end of the gripper arm back towards the main body of the catheter device; and pushing the leaflet anchor out of the leaflet anchor tube to pierce the leaflet from an atrial side and form the leaflet anchor into an unfolded configuration so that hooked formations of the leaflet anchor secure the leaflet anchor in the leaflet.

Viewed from a third aspect of the present invention, there is provided a method of manufacture of the catheter device of the first aspect, the method comprising forming the main body of the catheter device from an elastic material. The method may comprise forming the leaflet anchor tube in the main body of the catheter device. The method may comprise forming a hinge of the gripper arm integrally with the main body of the catheter device via cutting of an elastic metal tube. The method may include forming the entirety of the gripper arm, including the hinge, integrally with the main body. It is considered to offer particular benefits to be able to form the device of the first aspect in this way, although it should be noted that other manufacturing methods may be used as discussed above. A nitinol tube may be used and/or the cutting step may use laser cutting. The laser cut tube may be electropolished after cutting in order to remove any sharp edges.

Certain example embodiments of the invention will now be described by way of example only and with reference to the accompanying drawings in which.

Figure 1:
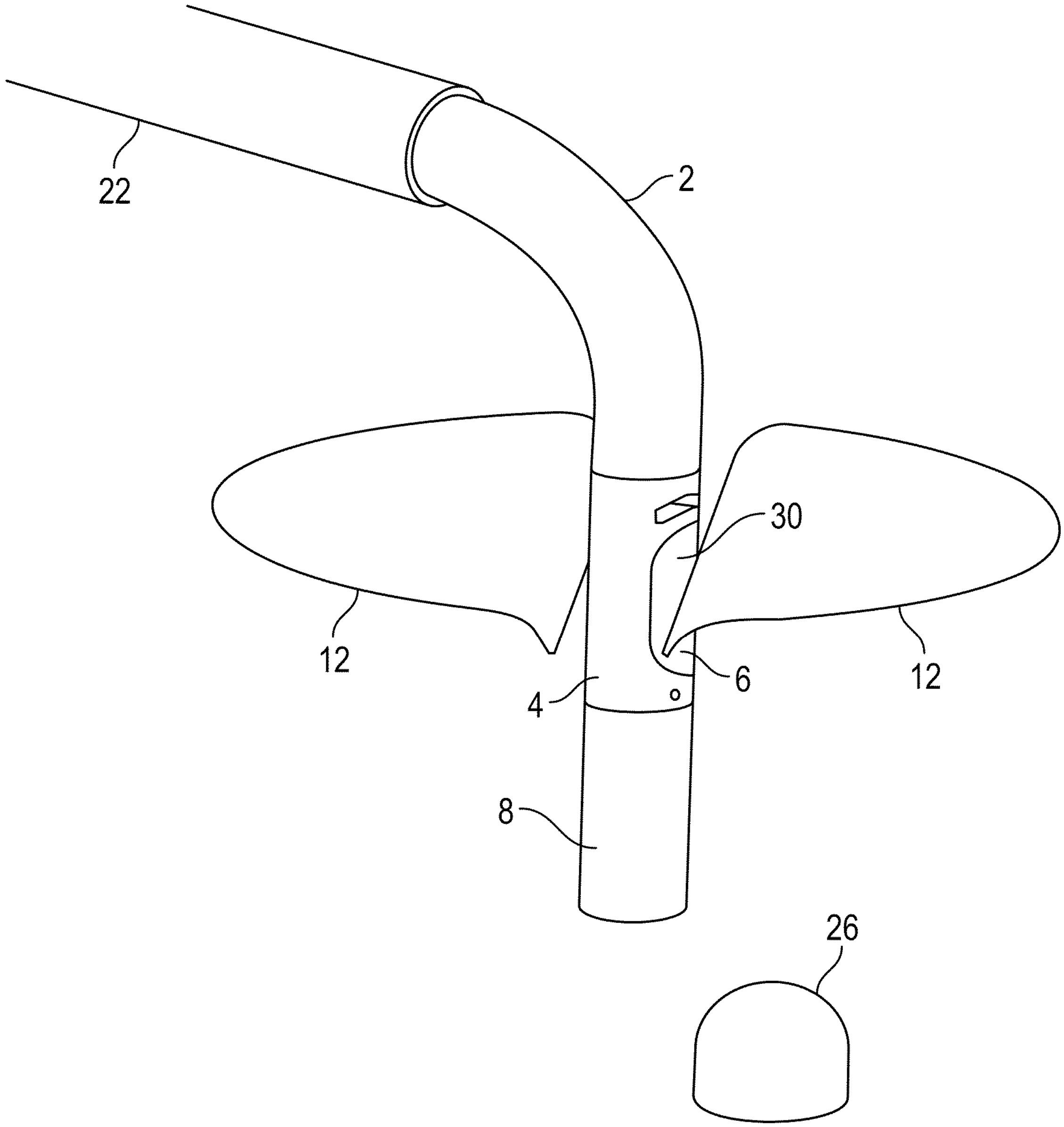
FIG. 1 illustrates the procedure for insertion of a catheter device through a mitral valve.

The catheter devices presented here are proposed for non-surgical (endovascular) insertion of mitral chords to address mitral regurgitation caused by prolapse of a leaflet 12 of the valve. The Figures show different forms of catheter device 2 for this purpose, but it will be understood that the general principles are the same for each device in terms of implantation of a leaflet anchor 10 and a papillary anchor 9 in order to insert one or more artificial chordae lines 14 into the heart. The artificial chordae line(s) 14 are fixed to the prolapsing leaflet 12 and to the papillary muscle 26, thereby recreating a normal anatomy. A single catheter device 2 is used to place both a leaflet anchor 10 and a papillary anchor 9. The length of the chord 14 can be adjusted, again using the same catheter device 2, to eliminate the mitral regurgitation. Thus, the new device enables a single minimally invasive endovascular procedure to be used to repair the mitral valve, providing significant advantages compared to earlier systems requiring more invasive procedures and/or multiple operations.

It should be noted that although an endovascular approach is preferred and the device is hence capable of using this approach, the device could of course be used in different procedures, including more invasive procedures. Many of the advantages will remain, and it could be beneficial to use this device in situations where a more invasive procedure is merited. In addition, it is contemplated that, as discussed above, aspects of the design of the papillary anchor 9 could be used for an anchor for other purposes and this disclosure is not intended to be limited in this regard.

The catheter device 2 described in the following can be used to insert mitral chords through the venous system, starting in the femoral vein in the groin. A catheter is advanced to the right atrium. Approach to the left atrium is then gained by a so-called transseptal puncture whereafter a larger guidance catheter is advanced into the left atrium. The catheter device 2 for the heart repair is then introduced through the guiding catheter and into the left atrium.

X-ray and ultrasound guidance is used to position the device and, as explained in more detail below, the mitral leaflet 12 is grabbed and an artificial chordae line 14 is attached using a self-expandable leaflet anchor 10. The artificial chordae line 14 is then attached to the papillary muscle 26, using a, papillary anchor 9. The chord length can now be adjusted to eliminate any mitral regurgitation. Excess chord is then cut and all catheters are withdrawn. Echo and Doppler imaging is used to perform the procedure and monitor the result. The successful use of this endovascular technique will drastically reduce the invasiveness, complications and cost of mitral valve repair.

More detail on the structure and function of the device is set out below with reference to the Figures. The procedure of using one form of the device can be summarised as follows:

1) The femoral vein is entered using standard Seldinger technique and the guiding catheter introduced.
2) The guiding catheter is advanced to the right atrium under x-ray guidance.
3) The left atrium is entered after penetration of the atrial septum, guided by x-ray and transesophageal echo.
4) Correct position of the entrance site in the left atrium is verified to assure proper alignment for insertion of the guiding and treatment catheters. The entrance hole in the atrial septum is dilated and the guiding catheter is advanced into the left atrium.
5) A treatment catheter device 2 is advanced through the guiding catheter and positioned in the left atrium above the mitral valve.
6) The prolapsing segment of the mitral leaflet 12 is located with ultrasound and the treatment catheter device 2 is advanced into the left ventricle placing a gripper 6 of the treatment catheter device 2 in position to grip the prolapsing segment.
7) The prolapsing segment is gripped and after assuring correct position the leaflet anchor 10 is pushed through the leaflet 12 allowing it to open and fix the leaflet 12.
8) The connection of the leaflet anchor 10 may be tested whilst it remains attached to the catheter device 2 via an ejector unit 36, and if the connection is sufficient then the distal end of catheter is advanced further into the left ventricle.
9) The papillary anchor 9 is pushed into the papillary muscle 26 area and out of its housing 8 thereby letting the papillary anchor 9 open inside the papillary muscle 26.
10) If the gripper 6 is still grasping the leaflet 12 then it is released, such as by releasing the leaflet anchor 12 from the ejector unit 36.
11) The length of the artificial chordae line 14 is adjusted until mitral regurgitation is eliminated.
12) The catheter device 2 is pulled back from the papillary anchor 9, and elimination of mitral regurgitation is again confirmed by echocardiography.
13) The position of the artificial chordae line 14 is locked at the papillary anchor 9.
14) The excess chordae line 14 is cut.
15) Additional artificial chordae lines may be placed if necessary.
16) The catheter device is fully withdrawn and removed from the vascular system.

FIGS. 1 to 19 display an exemplary catheter device 2 as disclosed by WO2020/109596. Whilst the catheter device 2 disclosed in WO2020/109596 is used to implant a leaflet anchor 9 in combination with an artificial chordae line 14 from a ventricular side of a mitral valve leaflet 12, many of the features and/or components of the exemplary catheter device 12 may be compatible with the catheter device 102 of the present invention, or may be modified in accordance with the teachings of the present invention such that a leaflet anchor 110 in combination with an artificial chordae line 114 can be implanted in a leaflet 12 from an atrial side of the leaflet 12.

FIG. 1 shows guide catheter 22 that has been used to steer a catheter device 2 to a required position within the heart adjacent extending through the mitral valve and hence being between two leaflets 12. The catheter device 2 is composed of four different main parts; a steerable catheter, a gripper housing 4, a gripper device 6 and a papillary anchor housing 8, which holds a papillary anchor 9. The gripper housing 4 and the papillary anchor housing 8 may form a proximal part 4 and a distal part 8 of a two part housing section with a central flexible and extendable joint 34 as shown in FIGS. 2 to 6, 14 and 20 to 22. Thus, it should be understood that the procedure shown in FIG. 1 (and likewise in FIGS. 7, 13 and 15) may use this arrangement for the gripper housing (proximal part) 4 and papillary anchor housing (distal part) 8. The steerable catheter could be replaced with an alternative arrangement using a steerable sheath about a steerable catheter and flexible tubing within the steerable catheter.

Figure 2:
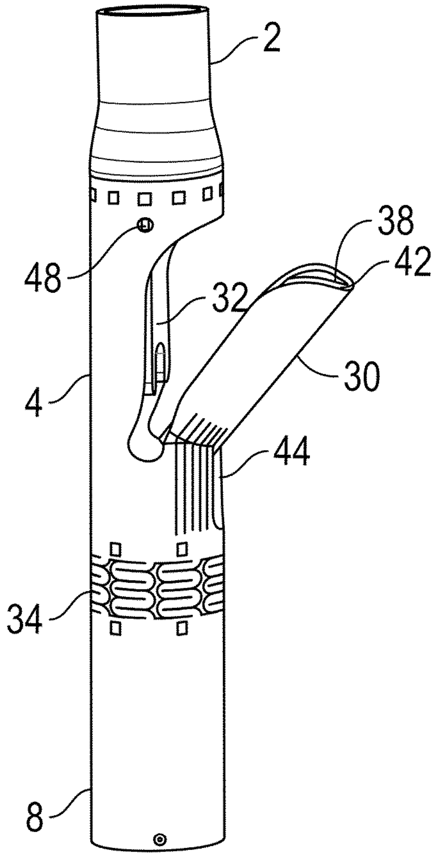
FIGS. 2 to 6 show the action of a mechanical gripping mechanism using two gripper arms.
Figure 3:
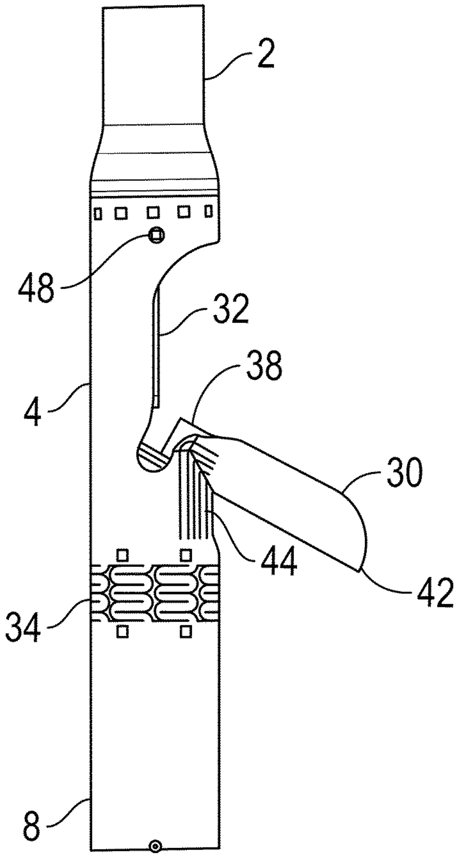
Figure 4:
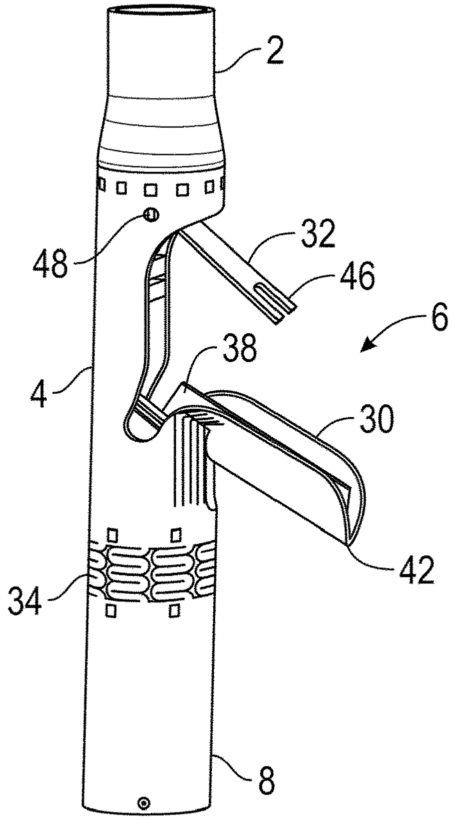
Figure 5:
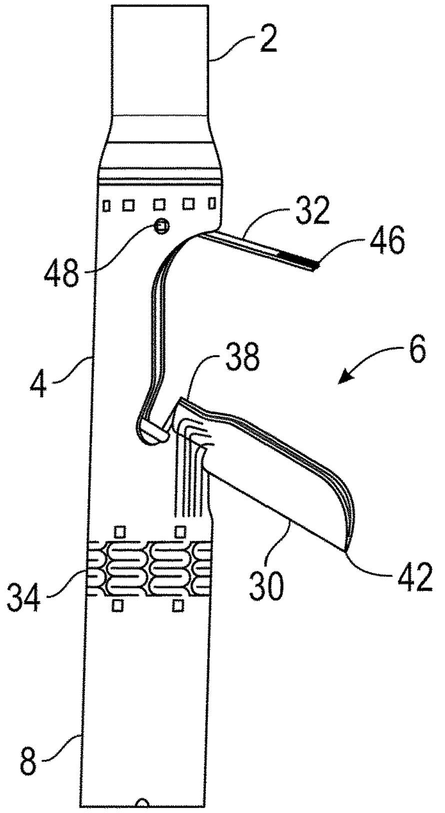
Figure 6:
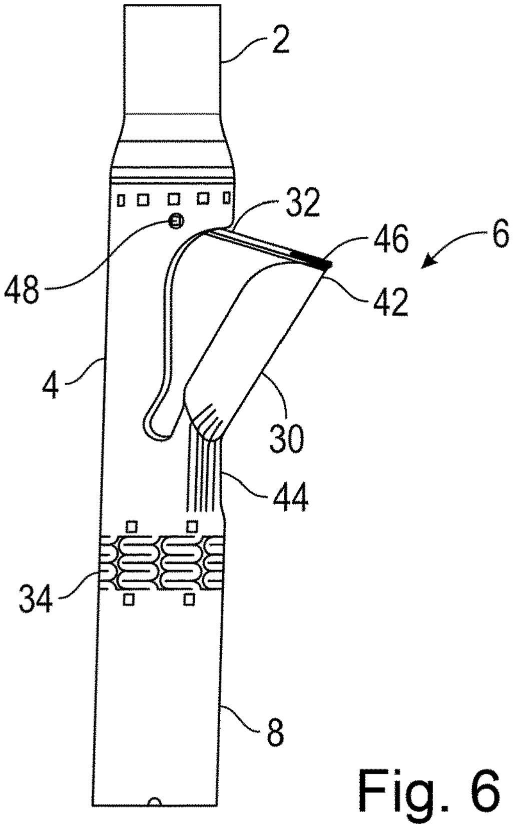
Figure 7:
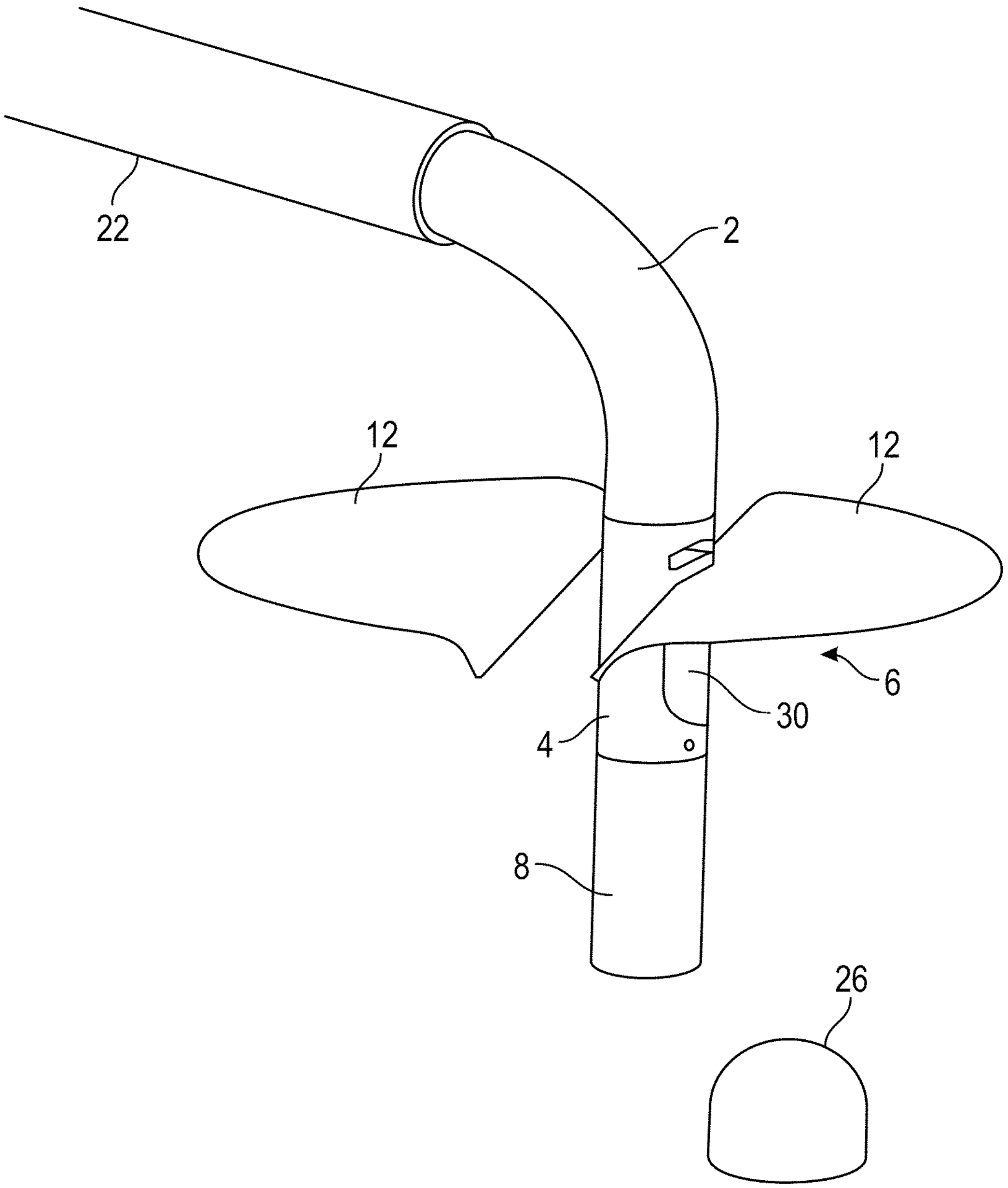
FIG. 7 illustrates gripping of a leaflet of the mitral valve with one gripper arm.

FIG. 1 shows a front view of one example catheter device with the gripper device 6 closed. The gripper device 6 of some arrangements uses a single gripper arm 30 that grips the leaflet 12 against the gripper housing part 4 as shown in FIG. 7. In other arrangements the gripper device 6 uses two gripper arms 30, 32 as shown in FIGS. 2 to 6 in order to allow the leaflet 12 to be grasped between the two gripper arms 30, 32 at a point spaced apart from the main body of the catheter device. The gripper device 6 is a part of a leaflet anchor deployment mechanism for deploying the leaflet anchor 10 to attach it to the leaflet 12 of the heart. The gripper device 6 includes a leaflet anchor tube 38 for housing the leaflet anchor 10 in a folded configuration prior to deployment. In the example embodiments the leaflet anchor tube 38 is in the (first) gripper arm 30, as seen in FIGS. 2 and 4, for example. When the gripper device 6 grasps the leaflet 12, the leaflet anchor 10 can be pushed out of the leaflet anchor tube 38 to pierce the leaflet 12 and form the leaflet anchor 10 into an unfolded configuration so that hooked formations 40 of the leaflet anchor 10 secure it in the leaflet 12.

Figure 20:
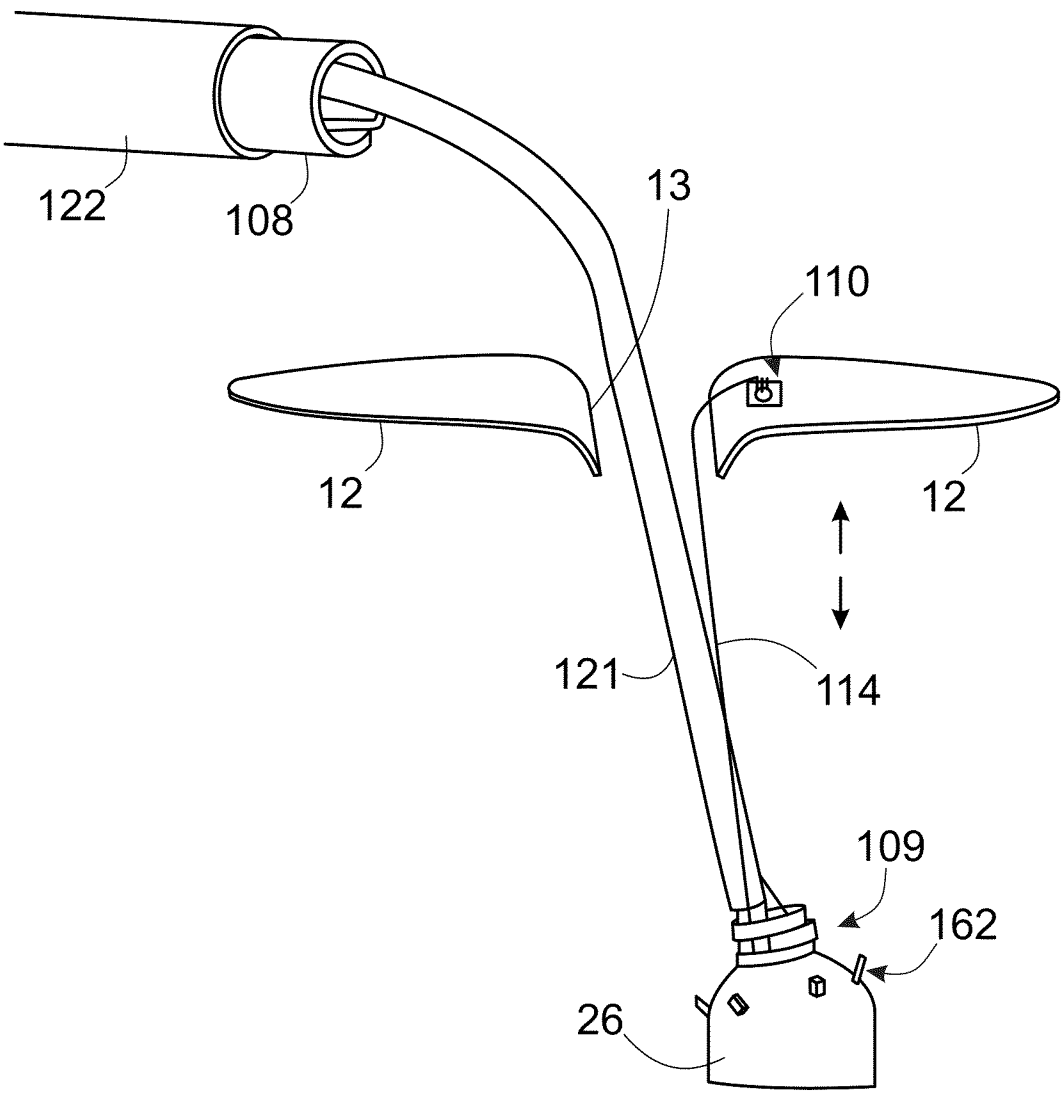
FIG. 20 illustrates withdrawal of a catheter device following implantation of a leaflet anchor in an atrial surface of a leaflet of a heart valve.
Figure 21:
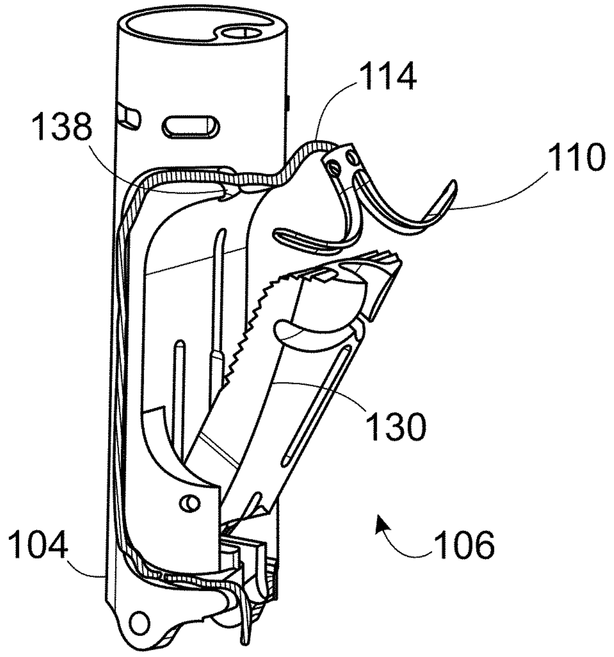
FIG. 21 shows the catheter device arranged to implant the leaflet anchor in the atrial surface of the leaflet of the heart valve.
Figure 22:
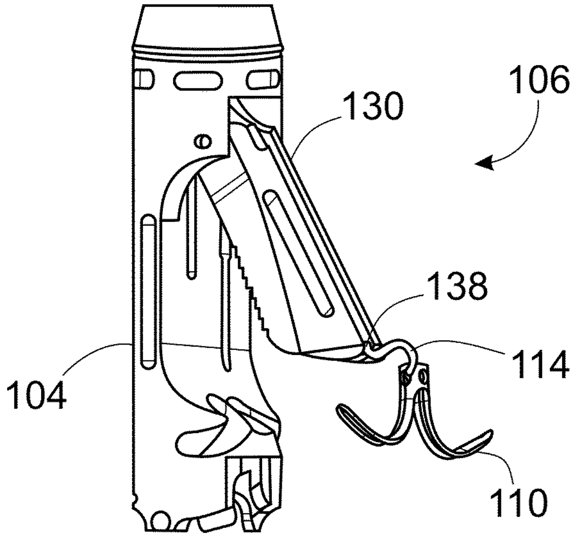
FIG. 22 shows an alternative arrangement of the catheter device arranged to implant the leaflet anchor in the atrial surface of the leaflet of the heart valve.

The leaflet anchor 10 is connected to an artificial chordae line 14, which can sit inside a narrow channel that goes along the surface of the first gripper arm 30 (as shown in FIGS. 8 to 12, for example) and via the papillary anchor housing 8 to the papillary anchor 9 (as shown in FIGS. 20 to 22, for example). The channel can be slightly smaller than the diameter of the artificial chordae line 14 and/or have a thin shielding structure (not shown). This makes the artificial chordae line 14 sit in place due to a friction fit. The artificial chordae line 14 goes into the papillary anchor housing 8 and through a papillary anchor locking section, through a locking and cutting piece. The artificial chordae line 14 can be attached to a wire which passes back along the catheter all the way to the outside (to make the adjustment smoother). The wire allows for a shortening of the chord during the procedure, by pulling, or a lengthening of the chord, since the wire can be pushed through the catheter.

The two-part housing section, with the gripper housing (proximal part) 4 and papillary anchor housing (distal part) 8 might be approximately 6-7 mm in diameter, and approximately 30 mm in length.

FIGS. 2 to 6 show steps in movement of the gripper mechanism 6 in an example with two gripper arms 30, 32 as discussed above. This gripper mechanism 6 is a part of a housing section that also includes a flexible and extendable joint allowing the papillary anchor housing 8 (distal part) to be moved toward the papillary muscle 26 after the leaflet 12 has been grabbed by the gripper mechanism 6. In this example, in order to grasp the leaflet 12, the first gripper arm 30 is rotated to move its end 42 away from the main body of the catheter device, with this rotation being enabled via a weakened area 44 of the tubular form of the main body. It can be seen that the leaflet anchor tube 38 sits inside the first gripper arm 30, with the end of the leaflet anchor tube 38 having an opening at the end 42 of the first gripper arm 30. With the first gripper arm 30 open, the second gripper arm 32 is free to rotate to move its end 46 outward of the main body. In this example the second gripper arm 32 rotates around a hinge formed by pins 48 placed in holes in the proximal part 4 of the two-part housing section, but it will be appreciated that a similar final placement of its end 46 may be achieved via a sliding movement. With the second gripper arm 32 folded outward the first gripper arm 30 can close so that the two ends 42, 46 come into contact at a point spaced apart from the main body of the device. This allows the leaflet 12 to be grasped. With the leaflet 12 in place the leaflet anchor 10 can be moved out of the leaflet anchor tube 38 to implant it, such as via a mechanism with an ejector unit 36 as described below in relation to FIGS. 8 to 12, with the final positioning of the leaflet anchor 10 being similar to that shown in FIG. 13.

FIG. 7 shows an alternative form of gripper mechanism 6 that grasps the leaflet 12 with a single gripper arm that holds it against the gripper housing 4. This could also use the ejector unit 36 mechanism of FIGS. 8 to 12.

A ridged surface on the gripper arm(s) 30, 32 may be provided to help it grip the leaflet 12. 3D ultrasound and/or other available sources can be used to confirm that the gripper mechanism 6 has grasped the correct part of the leaflet 12.

Figure 13:
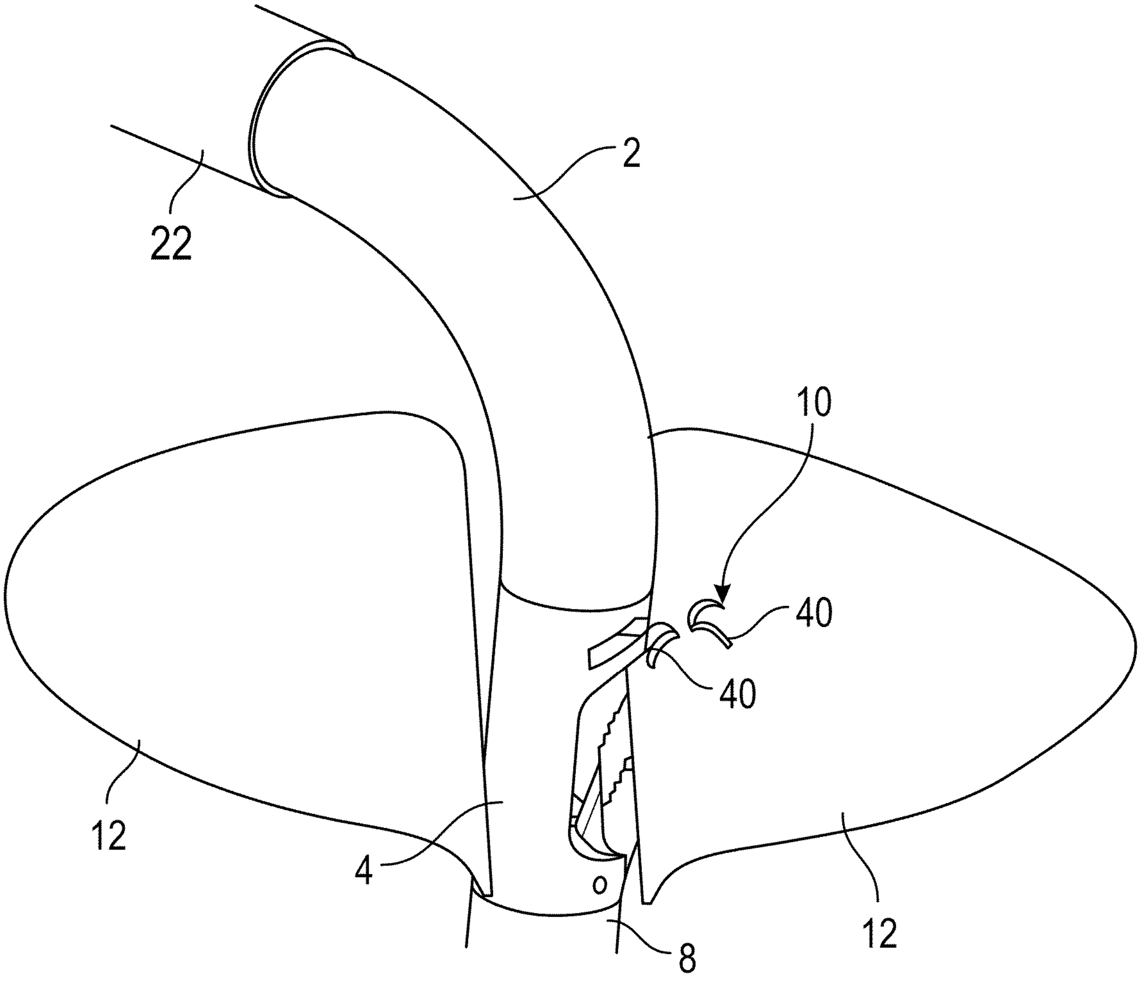
FIG. 13 shows a close up view of the valve during placement of a leaflet anchor, which is coupled to an artificial chordae line.

The gripper mechanism 6 can be opened and closed as many times as needed to grasp the right part of the leaflet 12. The opening and closing may be facilitated by a system allowing for one wire to pull the gripper mechanism 6 open, and one to pull it closed. Different arrangements of wires and/or rods may be used to control the example with two gripper arms 30, 32, as discussed above. Once the position of the gripper mechanism 6 is confirmed then the leaflet anchor 10 can be pushed out of the end of the leaflet anchor tube 38, such as by pulling a wire in the other end of the catheter. FIG. 13 shows a close up view of the leaflet anchor 10 placed in the leaflet 12 with the hooked formations 40 engaging with the leaflet 12.

Figure 8:
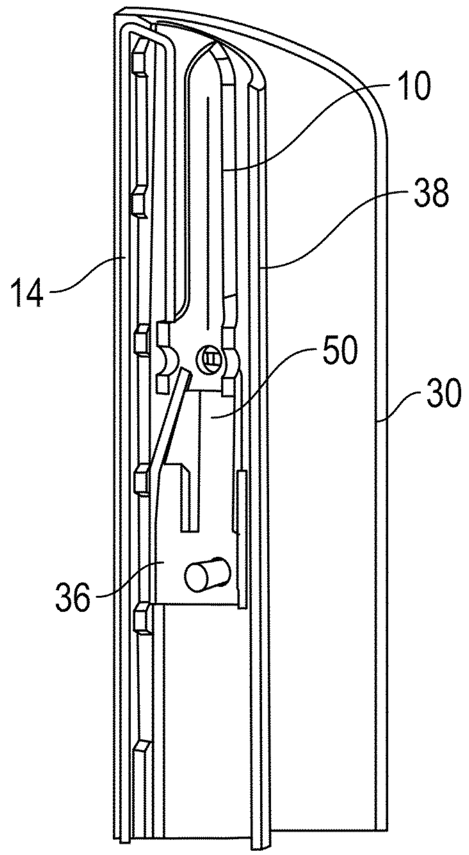
FIGS. 8 to 12 show deployment of a leaflet anchor in a device using an ejector device.
Figure 9:
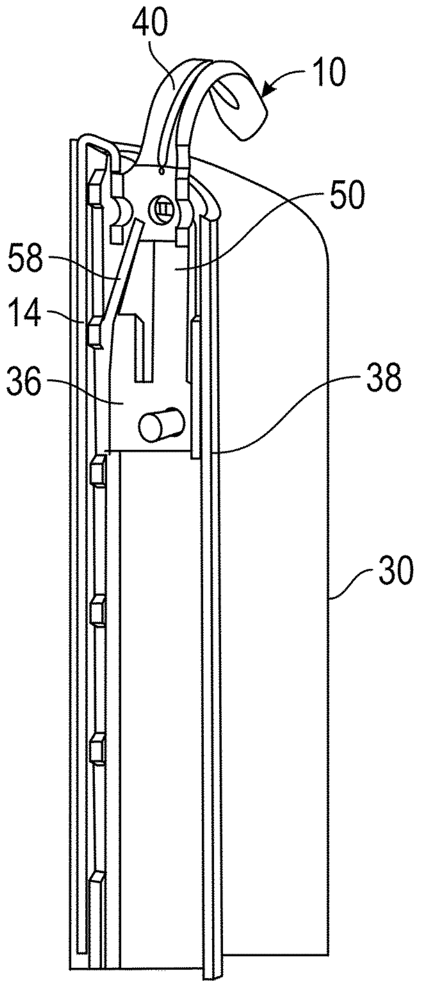
Figure 10:
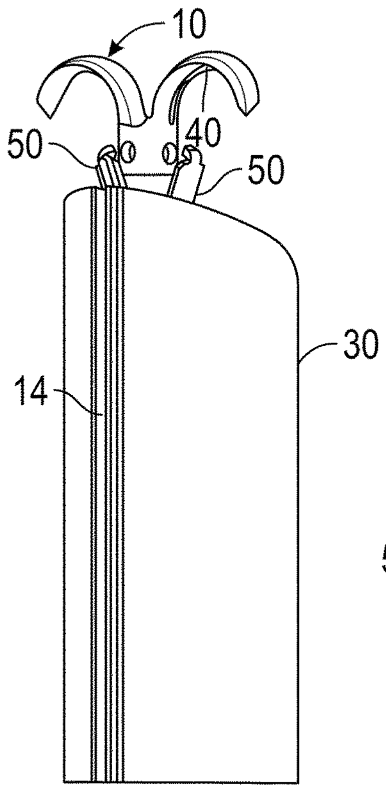
Figure 11:
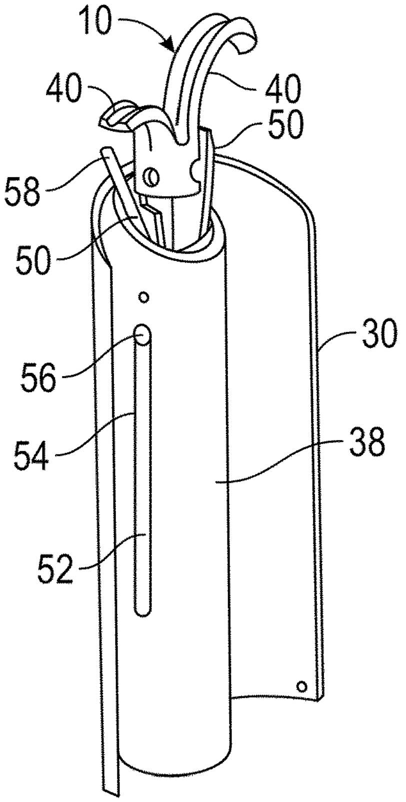

As noted above, an ejector unit 36 may be used as shown in FIGS. 8 to 12. With the use of the ejector unit 36 the leaflet anchor deployment mechanism allows for retraction and repositioning of the leaflet anchor 10 after deployment of the anchor 10 into the leaflet 12. This is achieved via the ejector unit 36, which includes a grasping device 50 with a first configuration, as shown in FIG. 8 and FIG. 9 and a second configuration as shown in FIG. 10 and FIG. 11.

In the first configuration the grasping device arranged to permit deployment of the leaflet anchor 10 into the leaflet 12 without disengagement of the leaflet anchor 10 from the ejector unit 36. Thus, the grasping device 50, which in this example comprises two grappling hooks 50 as shown, grips the leaflet anchor 10 and can advance along the leaflet anchor tube 38 from the fully stowed position as in FIG. 8, to a position in which the anchor 10 is deployed as shown in FIG. 9, without releasing the anchor 10. The grappling hooks 50 are held to the leaflet anchor 10 as they are constrained within the leaflet anchor tube 38. The ejector unit 36 is hence arranged so that it remains in the first configuration whilst the leaflet anchor 10 is being implanted. With the leaflet anchor 10 implanted the grasping device 50 and ejector unit 36 can be used to test the connection of the leaflet anchor 10 to the leaflet 12, for example by a force being applied to the leaflet anchor from the ejector unit whilst the grasping device 50 is in the first configuration.

The grasping device 50 moves into the second configuration when the constraint from the leaflet anchor tube 38 is no longer present, for example when the grappling hooks 50 move beyond the end of the tube as shown in FIG. 10. Thus, if the connection has been tested and the physician decides to release the leaflet anchor 10 then they can further advance the ejector unit 36, which will move it into the second configuration. In this second configuration the grasping device 50 of the ejector unit 36 is disengaged from the leaflet anchor 10.

If the physician is not satisfied by the connection during the testing (for example, if there is too much movement of the anchor 10 and/or not enough resistance to force on the line) then the leaflet anchor 10 can be retracted and placed in another location. If the grasping device 50 did not change from the first configuration during this test then the latter procedure may be carried out by reversing the deployment of the ejector unit 36 and leaflet anchor 10, for example by drawing those parts back into the leaflet anchor deployment mechanism. If the second configuration was used before it was determined that the connection of the anchor was not adequate then to retract the anchor 10 the ejector unit 36 should be first moved back to the first configuration so that the grasping device 50 reengages with the leaflet anchor 10, and then after that the deployment of the ejector unit 36 and leaflet anchor 12 is reversed, for example by drawing those parts back into the leaflet anchor tube 38.

A groove 52 is provided in a wall of the leaflet anchor tube 38 for guiding the ejector unit 36. The groove 52 ensures that the ejector unit 36 remains a single orientation relative to the tube 38 while it is moved along the tube. The groove 52 can set maximum limits on the range of movement of the ejector unit 36 and thus may prevent it from going too far in either direction, out of or into the leaflet anchor tube 38. The ejector unit 36 has a guide pin 56 for engagement with the groove 52. A narrowing 54 in the groove 52 is provided to act as an indicator to let the operator know when the ejector unit 36 has reached a certain position. The size of the guide pin 56 and the width of the narrowing 54 are set so that engagement of the pin 56 with the narrowing 54 in the groove 52 will require an increased force before further movement can be made, thus providing tactile feedback to the operating physician.

The leaflet anchor deployment mechanism of FIGS. 8 to 12 also includes a line pusher 58 for directing the artificial chordae line 14 out of and away from the leaflet anchor tube 38 during deployment of the anchor 10. The line pusher 58 directs the artificial chordae line away from the leaflet anchor tube 38 so that it can be more readily accessed for later manipulation, such as for tightening the line 14 or for pulling on the implanted leaflet anchor 10 for testing of the connection. The line pusher 58 is actuated during the action of deployment of the leaflet anchor 10, with this actuation being triggered when the leaflet anchor 10 is released from the ejector unit 36. Thus, the line pusher 50 is released when the ejector unit 36 withdraws away from the implanted leaflet anchor 10.

Figure 12:
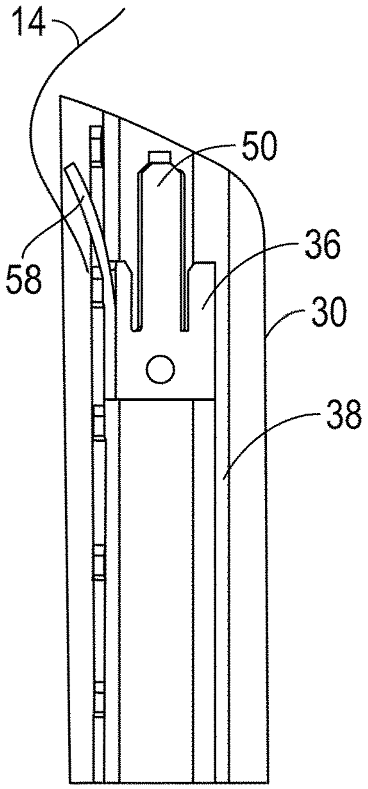

In the example shown, the line pusher 58 transitions from a constrained state to a non-constrained state and moves radially outward to push the line 14 out, with this radially outward movement being permitted and the line pusher released once a constraint from the leaflet anchor 10 is removed. The line pusher 58 is an arm that extends axially forward from the ejector unit toward the leaflet anchor 10 and radially outward of the leaflet anchor tube 38 when the arm is at rest with no forces applied. Prior to deployment of the leaflet anchor 10 the arm of the line pusher 58 is bent elastically to place its distal end within the leaflet anchor 10, as shown in FIGS. 8 and 9, so that it is constrained and cannot move to its radially outward position until the leaflet anchor 10 and the ejector unit 36 move apart, as is best shown in FIG. 11. As the ejector unit 36 continues to withdraw into the leaflet anchor tube 38 the line pusher 58 remains in its unconstrained state with the line pusher 58 as well as the line 14 being pushed out of a slit in the leaflet anchor tube 38, as shown in FIG. 12.

Figure 14:
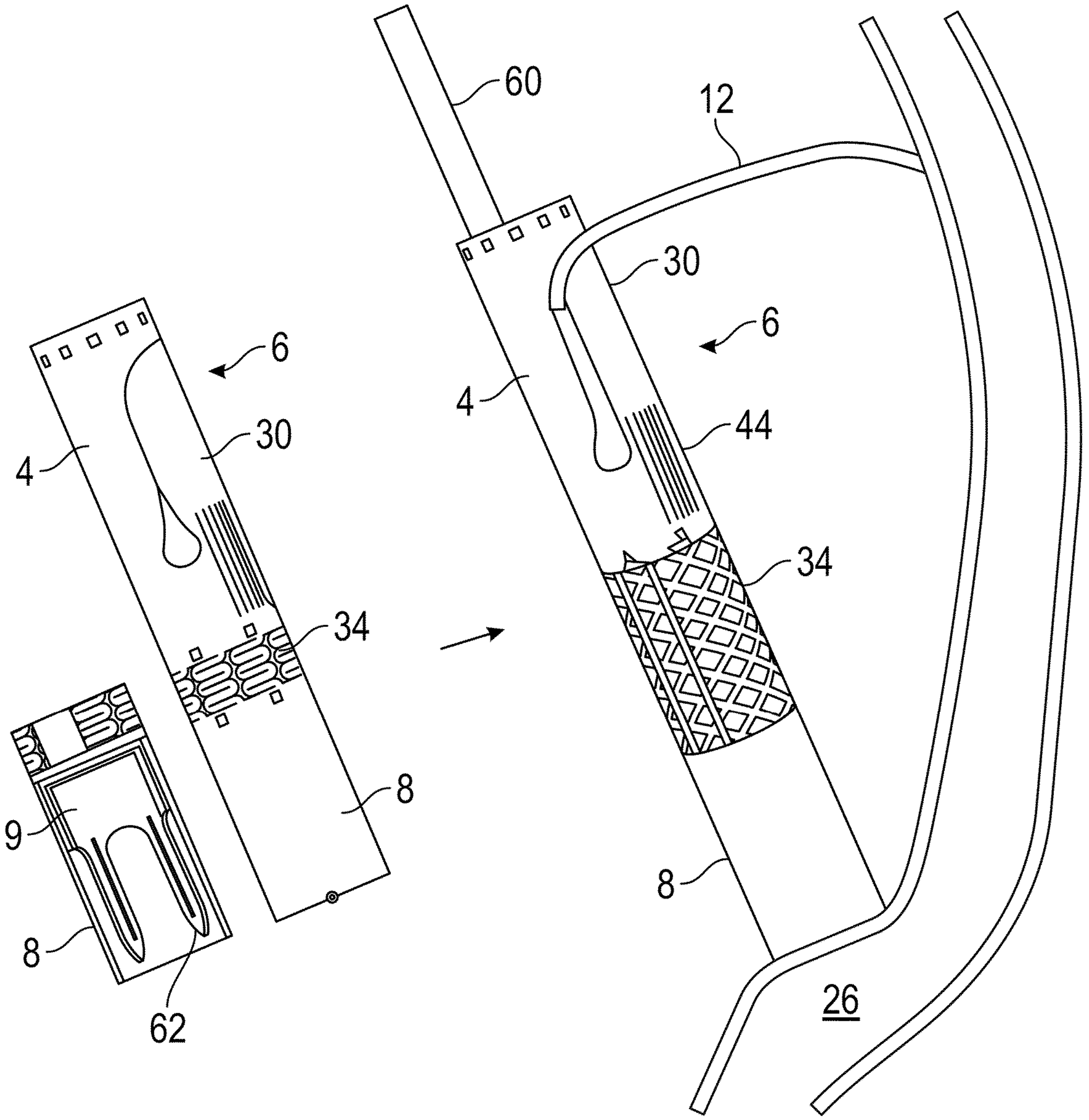
FIG. 14 shows movement of the distal end of the catheter device to the papillary muscle for placement of a papillary anchor.

With the leaflet anchor 10 implanted in the leaflet 12 the papillary anchor housing 8 at the end of the treatment catheter is then placed onto the papillary muscle 26. With the use of a flexible and extendable joint 34 this may be done as shown in FIG. 14. In this example, the flexible and extendable joint 34 is formed by flexible meandering sections cut into a tubular form of the main body. The flexible and extendable joint 36 is formed integrally with a tubular distal part 8, which provides the papillary anchor housing 8 and with a tubular proximal part 4, which provides the gripper housing 4. Further the tubular form of the gripper housing 4 may include an integrally formed gripper arm 30, with a weakened section 44 of the tube providing a hinge. The flexible and extendable joint 34 can be extended by means of wires and/or rods 60 (or via an adjustment catheter 21, that also may push out the papillary anchor 9), which may apply a force to stretch elastic elements of the joint 34. This extension is used to move the papillary anchor 9, within its housing part 8, to place it against the papillary muscle 26, or close to it, since the wires/rods along with the papillary anchor 8 within the distal housing part 8 move with the housing 8 as the joint 34 extends. This can be due to friction between the papillary anchor 9 (or a papillary anchor push tube) and the internal surface of the distal part 8 of the housing section. The position can be confirmed by 3D ultrasound and/or other available sources.

When the distal end of the distal part 8 meets the body tissue, and as further force is applied the counterforce from the body tissue eventually surpasses the forces holding the papillary anchor 9 in place, at this point tissue is pushed flat below the base of the distal part 8 giving a maximal chance of placing all pins 62 of the papillary anchor 9 correctly in tissue, and force can be applied to the papillary anchor 9 so that the ends of the pins 62 then move beyond the distal end of the distal part 8 to meet the body tissue. This may be done via additional force on the papillary anchor 9 from rods or wires 60 or extending the adjustment catheter 21, or it may be done through a pre-tension on the papillary anchor 9 (or friction between the adjustment catheter 21 and the distal part 8) that is held by friction with the distal part until the forces from the body tissue on the distal part 8 changes the balance of forces with the friction sufficiently so that the papillary anchor 9 ejects in a way similar to a paper stapler. As the papillary anchor 9 is ejected the pins 62 fold out and form into the hook shape of the unconstrained papillary anchor 9 to thereby engage with the body tissue 26. At this point the connection can be pull tested by operator, and/or visually confirmed on x-ray and/or ultrasound. If the connection is not satisfactory, the papillary anchor 9 can be pulled back into the distal part 8 and re-placed to attempt an improved coupling of the anchor 9 with the body tissue 26.

Figure 15:
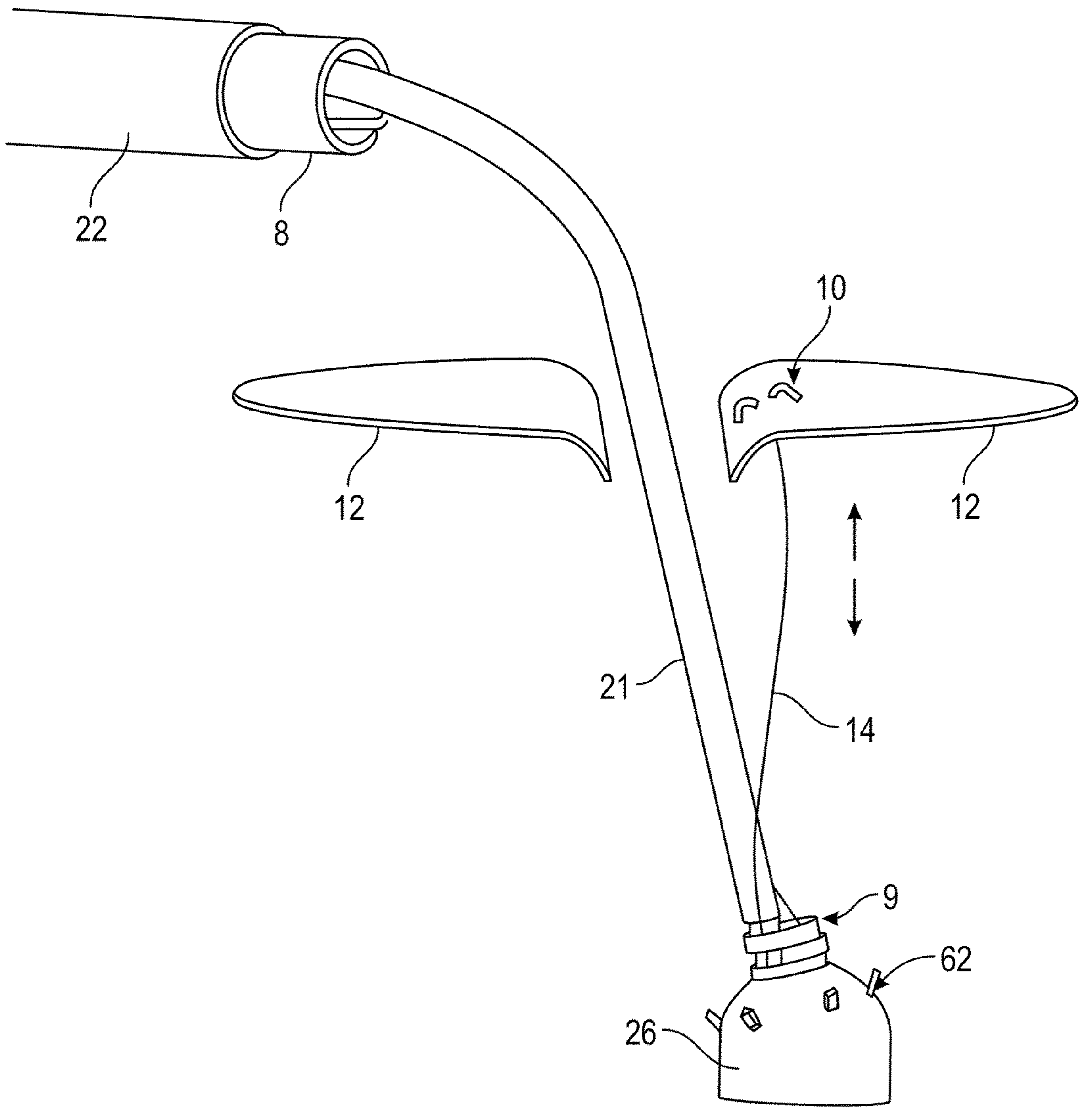
FIG. 15 illustrates withdrawal of a treatment catheter part of the device and adjustment of the chord length with an optional adjustment catheter.

FIG. 15 shows the possible next steps. The main part 4, 8 of the device is retracted to minimize influence on the moving leaflets 12. An adjustment catheter 21 can remain at the papillary anchor 9. The length of the artificial chordae line 14 can be adjusted with a wire from the outside. The length is continuously adjusted and the functioning of the leaflet 12 is monitored. The length of the artificial chordae line 14 can be reduced by pulling the chord wire back through the catheter. The length can also be increased by pushing the chord wire, which will slacken the artificial chordae line 14 and allow the movement of the leaflet 12 to pull it out of the adjustment catheter 21. The small size of the adjustment catheter 21 means that the effect of the device on the functioning of the leaflet 12 is minimised. The right length for the artificial chordae line 14 is confirmed with 3D ultrasound and/or other available sources.

When the correct length is confirmed then the device is disengaged from the papillary anchor 9. This process also locks the artificial chordae line 14 in place and cuts off any excess, which is retained in the catheter and withdrawn from the body when the catheter is removed. A locking segment 28 of the papillary anchor 9 is held open by the cutting piece (not shown). The locking segment 28 is a band of the papillary anchor 9 that can be flexed to open a gap for the artificial chordae line 14 to pass through. In the natural shape of the papillary anchor 9, when no force is applied, this locking segment 28 fits closely with the remainder of the anchor 9 and so it will hold the artificial chordae line 14 in place. The locking segment 28 is held open until the artificial chordae line 14 is the correct length. The cutting piece cuts the artificial chordae line 14, which is pulled against the blade when the adjustment process is completed.

Figure 16:
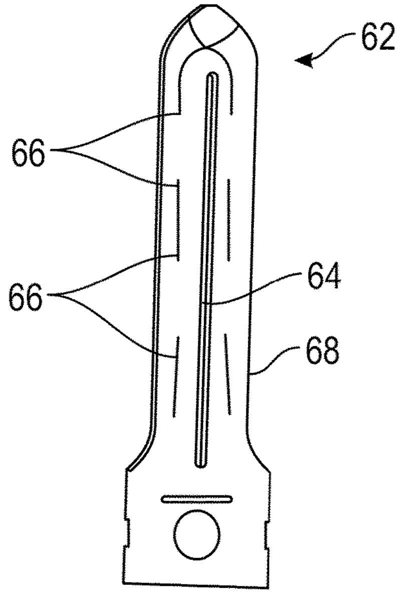
FIGS. 16 and 17 show an example of a hook for an anchor which is threaded with a suture.
Figure 17:
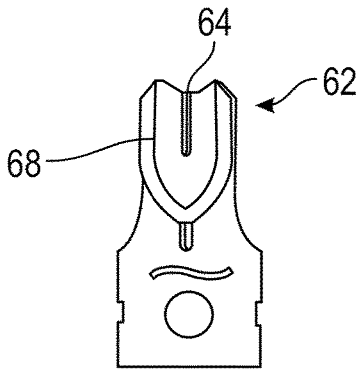

FIGS. 16 to 19 include more details of the papillary anchor 9, including its hooks 62 which are formed by curving pins 62. FIGS. 16 and 17 show one possible form for the hooks 62, with a central slit 64 and a series of holes 66 threaded with a suture 68. As discussed above, this suture 68 and the holes 66 can allow the hooks 62 to better engage with body tissue during healing, as well as keeping the material of the hooks 62 connected to the main body of the papillary anchor 9 in the event of a breakage. FIG. 16 shows the folded/constrained shape of the hook 62, which is also the shape of a tine formed in a tubular section during manufacture of the anchor 9, prior to heat setting to form the curve. FIG. 17 shows the curved form of the hook 62, i.e. the unfolded/unconstrained form.

Figure 18:
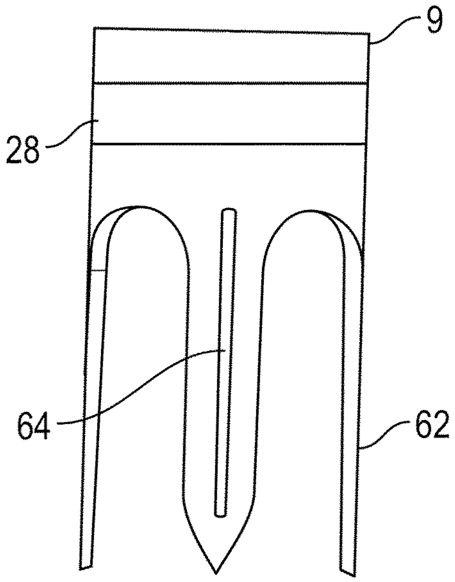
FIGS. 18 and 19 show the folded and unfolded configuration of an example of a papillary anchor.
Figure 19:
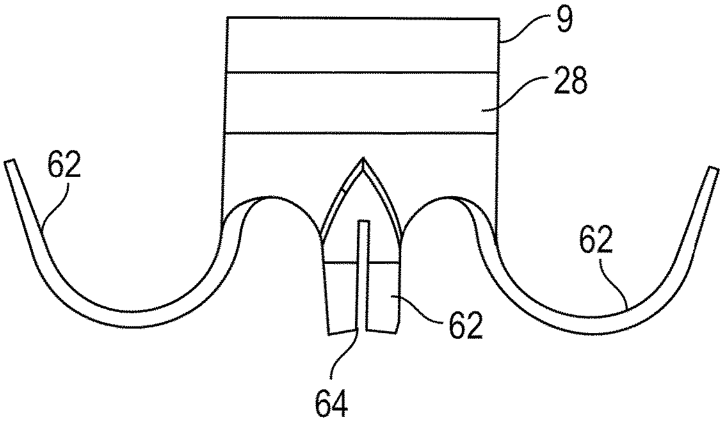

FIGS. 18 and 19 show an example of an entire papillary anchor 9, again illustrating the folded (FIG. 18) and unfolded (FIG. 19) configurations. This papillary anchor 9 includes hooks 62 with an opening in the form of a slit 64, which may result in better engagement with the body during healing as well as increased surface area without loss of flexibility.

The catheter device 2 disclosed in each of WO2016/042022 and WO2020/109596 implants the leaflet anchor 10 from a ventricular side of the leaflet 12. As shown in FIG. 15, the artificial chordae line 14 therefore descends from the leaflet 12 from a ventricular surface of the leaflet 12 to the papillary muscle 26. A number of benefits are associated with implanting the leaflet anchor 10, and hence the artificial chordae line 14, in a ventricular side of the leaflet 12, as discussed in each of WO2016/042022 and WO2020/109596.

However, there may be situations in which it is advantageous to implant a leaflet anchor 110, and hence an artificial chordae line 114, from an atrial side of the leaflet 12. For example, as can be seen in FIG. 15 the artificial chordae line

14 descends to the papillary muscle 26 without providing any additional support to an edge 13 of the leaflet 12. When implanted from a ventricular side of the leaflet 12, the artificial chordae line 14 does not provide additional support to the edge 13 of the leaflet 12. The implanted artificial chordae line 14 may therefore not replicate the action of chordae tendineae located towards the edge 13 of the leaflet 12 as accurately as desired.

Implanting the leaflet anchor 10 from a ventricular side of the leaflet 12 also requires a more precise placement of the leaflet anchor 10. As there is no additional support provided to the edge 13 of the leaflet 12, the placement of the leaflet anchor 10 will determine to what extent the edge 13 of the leaflet 12 is supported and/or secured by the leaflet anchor 12. In contrast, the placement of a leaflet anchor 110 implanted from the atrial side of the leaflet 12 can be less precise, since the artificial chordae line 114 will provide additional support to the edge 13 of the leaflet 12 as it passes into the ventricle from the atrium of the heart.

The present invention provides a modified catheter device 102 capable of implanting a leaflet anchor 110 from an atrial side of the leaflet 12, as will now be described in detail.

FIG. 20 shows the withdrawal of a guide catheter 122 and a distal part 108 of a catheter device 102 once an artificial chordae line 114 has been implanted in the papillary muscle 26 using a papillary anchor 109, and once the artificial chordae line 114 has also been implanted in the leaflet 12 of the heart using a leaflet anchor 110. The adjustment catheter 121 is shown in place before its withdrawal. The length of the artificial chordae line 114 can be adjusted as necessary in the illustrated configuration.

FIG. 20 is similar to the arrangement shown in FIG. 15, but shows the leaflet anchor 110 implanted from an atrial side of the leaflet 12 rather than a ventricular side. As can be seen in FIG. 20, the artificial chordae line 114 extends from a base of the leaflet anchor 110 where it is attached towards the leaflet edge 13. As the artificial chordae line 114, when under tension or otherwise, will take the shortest possible path to the papillary muscle 26 where the other end is implanted, the artificial chordae line 114 will be in contact with the atrial side surface of the leaflet 12 and will descend, in contact, over the edge 13 of the leaflet 12. As such, the artificial chordae line 114, implanted in an atrial side of the leaflet 12, will provide additional support to the edge 13 of the leaflet 12.

The artificial chordae line 114 can comprise regions of varying cross-sectional area along its length. By increasing the cross-sectional area of the artificial chordae line 114 in certain sections, the artificial chordae line 114 can have an increased area of contact with the leaflet 12 of the heart. As such the force applied by the artificial chordae line 114 to the leaflet 12 may be more evenly distributed, and any pinching of the leaflet 12 which the artificial chordae line 114 may cause can be avoided.

The artificial chordae line 114 comprises a flattened cross-section proximal to the leaflet 12, i.e. such that a major axis of the cross-sectional area of the artificial chordae line 114 lies parallel to the surface of the leaflet 12. In alternative arrangements, the artificial chordae line 114 can be formed of a plurality of sutures, such that an area of contact between the artificial chordae line 114 and the atrial surface of the leaflet 12 is increased.

To implant the leaflet anchor 110 in the leaflet 12 of the heart from an atrial side, a leaflet anchor deployment mechanism and a gripper housing 106 of the catheter device 102 are arranged as shown in either FIG. 21 or FIG. 22.

FIG. 21 shows the catheter device 102 comprising a gripper housing 106, a gripper arm 130 and the artificial chordae line 114 attached to the leaflet anchor 110 and routed through the main body of the catheter device 102. The leaflet anchor 110 is housed in the main body of the catheter device 102, and is deployed by pushing it out of a leaflet anchor tube 138 located in the main body of the catheter device 102. The leaflet anchor tube 138 is similar in function to the leaflet anchor tube 38 described above. The leaflet anchor tube 138 is located in the main body of the catheter device 102 such that when the leaflet 12 is grasped between the gripper arm 130 and the main body of the catheter device 102 (similarly to as shown in FIG. 7), the leaflet anchor 110 can be deployed from the anchor tube 138 into an atrial side of the leaflet 12. The leaflet anchor 110 will hence be deployed in the leaflet 12 as shown in FIG. 20.

FIG. 22 shows an alternative arrangement of the catheter device 102 comprising a gripper housing 106, a gripper arm 130 and the artificial chordae line 114 attached to the leaflet anchor 110. Whilst not shown, the artificial chordae line will be routed through the gripper arm 130 and the main body of the catheter device 102 such that the artificial chordae line 114 can be deployed from the catheter device 102, once the line 114 is adjusted following implantation. The leaflet anchor 110 is housed in a leaflet anchor tube 110 located in the gripper arm 130, with an opening of the leaflet anchor tube 138 located at a distal end of the gripper arm 130. So that the leaflet anchor 110 can be deployed in an atrial side of the leaflet 12 as shown in FIG. 20, the gripper arm 130 is rotated from a proximal end of the catheter device 102, so that the opening of the leaflet anchor tube 138 will be located adjacent to the atrial side surface of the leaflet 12.

In both of the arrangements as shown in FIGS. 21 and 22, the components of the catheter device 102 may function similarly to those described in relation to FIGS. 1 to 19. The leaflet anchor tube 138 will generally operate similarly to the leaflet anchor tube 38 discussed in relation to FIGS. 8 to 12. The gripper device 106 will function similarly to the gripper device 6 as discussed in relation to FIGS. 2 to 6. The leaflet anchor 110 will be similar to the leaflet anchor 10 discussed in relation to FIGS. 8 to 12, 16 and 17. The papillary anchor 109 will be similar to the leaflet anchor 9 discussed in relation to FIGS. 14, 15, 18 and 19.

In both of the arrangements shown in FIGS. 21 and 22 and as discussed above, the leaflet anchor tube 138 extends in a direction along the main body of the catheter device 102 or the gripper arm 130 such that the opening of the leaflet anchor tube 138 opens towards a distal end of the catheter device 102. As the catheter device 102 approaches the leaflet 12 and the papillary muscle 26 from above the leaflet 12 and the papillary muscle, i.e. from the left atrium as discussed above, the opening of the leaflet anchor tube 138 is therefore arranged to meet the atrial surface of the leaflet 12, such that the leaflet anchor 110 can be implanted in the atrial surface of the leaflet 12.

The catheter devices taught in each of WO2016/042022 and WO2020/109596 used a U-rod to deploy the leaflet anchor. However, the catheter device 102 employs a linear rod to deploy the leaflet anchor 110. The linear rod will extend from a proximal end of the catheter device 102 and into the leaflet anchor tube 138, such that the leaflet anchor 110 can be deployed into the atrial side of the leaflet 12. The linear rod deploys the leaflet anchor 110 by pushing the leaflet anchor 110 out of the distally-facing opening of the leaflet anchor tube 138, using the end of the linear rod located in the leaflet anchor tube 138. The linear rod is flexible so that it can curve or bend, e.g. from the main body of the catheter device 102 shown in FIG. 22 and into the gripper arm 130 when flexed, and is tensile so that it can be pushed into and retracted from the leaflet anchor tube 138 without elongating. When the leaflet anchor tube 138 is located in the gripper arm 130 as shown in FIG. 22, the elastic properties of the linear rod can help restore the gripper arm 130 to the closed position, i.e. flush to the main body of the catheter device. The linear rod is made of a material with the ability to deform elastically to a high degree in order to allow for the bending of the bendable section. Suitable materials include shape memory materials, for example shape memory metals such as nitinol. Using a shape memory metal also means that the linear rod can be made to be stiff, which makes the transfer of force with the linear rod more efficient. Alternatively, the linear rod could be made of several types of materials to achieve the required properties.

Whilst the following features will be discussed in relation to the catheter device 102 as discussed in relation to FIGS. 20 to 22, it will be appreciated that the following features are similarly compatible with the catheter device 2 as discussed in relation to FIGS. 1 to 19 and as disclosed in each of WO2016/042022 and WO2020/109596.

Figure 23A:
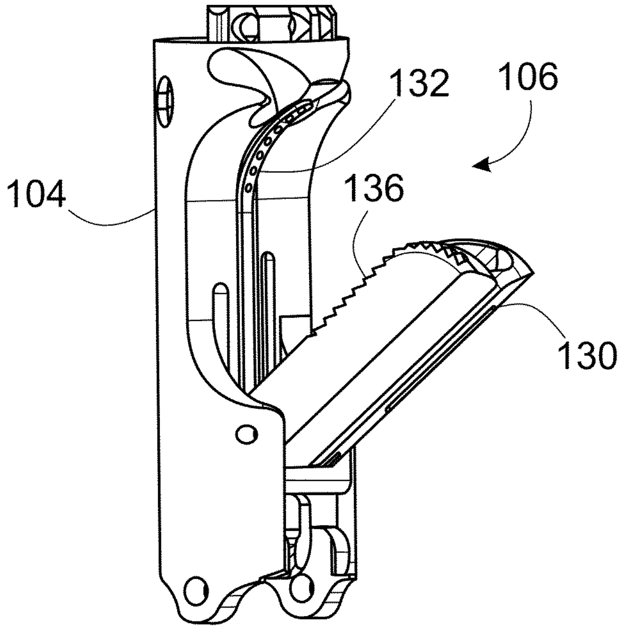
FIG. 23A shows a modified gripper device for grasping the leaflet of the heart valve in an undeployed configuration.
Figure 23B:
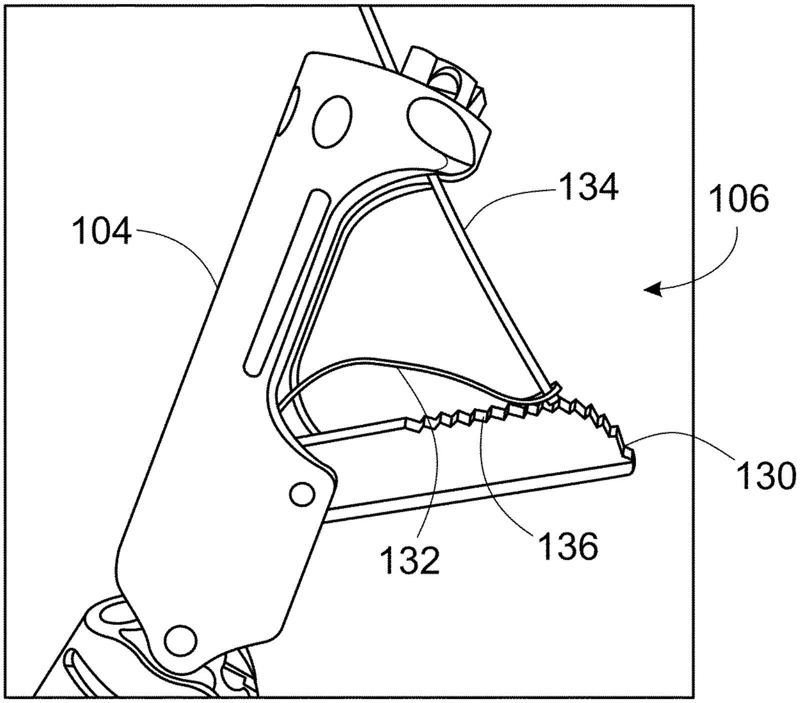
FIG. 23B shows the modified gripper device for grasping the leaflet of the heart valve in a deployed configuration.

FIGS. 23A and 23B show an alternative arrangement for the gripper device 106. The gripper device 106 comprises the gripper arm 130 in combination with a gripper lever 132. The gripper lever 132 is biased such that at rest, i.e. in an undeployed configuration, the gripper lever will sit flush to the main housing of the catheter device 102 as shown in FIG. 23A. The gripper lever 132 is located between the gripper arm 130 and the main body of the catheter device 102, such that the gripper lever 132 cannot be actuated away from the main body of the catheter device 102 without first opening the gripper arm 130 as shown in FIG. 23B.

The gripper lever 132 is fixed at an end adjacent to where the gripper arm 130 is rotated from. The other end of the gripper lever 132 is free to move relative to the main body of the catheter device 102. The free end of the gripper lever 132 is attached to a wire or rod 134 which runs through the main body of the catheter device 102 and pushes the free end of the gripper lever 132. When pushed, the rod 134 therefore actuates the gripper lever 132 such that it is in a deployed configuration. In the deployed configuration, free end of the gripper lever 132 is arranged to meet the gripper arm 130. Thus, when in use, the leaflet 12 can be grasped between the gripper arm 130 and the gripper lever 132.

The combined grasping action of the gripper arm 130 and the gripper lever 132 can help ensure that the leaflet 12 is correctly grasped. The gripper arm 130 can be opened so that a gripping surface 136 of the gripper arm 130 meets the leaflet 12. Without additional support the leaflet 12 may move away from the gripper arm 130 as the gripper arm 130 is closed, due to the motion of the leaflet 12 during the cardiac cycle. However, the present arrangement of the gripper device 106 deploys the gripper lever 132 before the gripper arm 130 is closed. The leaflet 12 is therefore secured between the gripper lever 132 and the gripper arm 130 before the gripper arm 130 is closed. Finally, the gripper lever 132 and the gripper arm 130 can be withdrawn, with the leaflet 12 still secured, so that the leaflet 12 is secured in the desired position between the gripper arm 130 and the main body of the catheter device 102 when the gripper arm 130 is in the closed position. The leaflet anchor 110 can then be deployed in the desired location. Thus the provision of the gripper lever 132 may help increase the likelihood of successfully grasping the leaflet 12, and may ensure the correct positioning of the leaflet anchor 110 in the leaflet 12 during implantation of the leaflet anchor 110.

The gripper lever 132 can include a number of indentations or teeth along its length, which may assist in grasping the leaflet 12. The indentations or teeth increase the frictional hold of the gripper lever 132, such that the leaflet 12 is less likely to accidentally release from the gripper arm 130 and the gripper lever 132 when grasped. The gripper lever 132 is generally flexible so that it can be held at the end at which the gripper arm 130 is rotated from and can be pushed at the free end by the rod 134 to meet the gripper arm 130. The gripper lever 132 and the rod 134 may each be formed of a suitable elastic, yet tensile, material such as nitinol or stainless steel. The gripper lever 132 can be secured to the main body of the catheter device 102 and the rod 134 by welding or gluing the components together.

Whilst the gripper lever 132 has been described herein as being flush to the main body of the catheter device 102 when unconstrained, and contacting the gripping surface 136 when in the rod 134 is actuated, the gripper lever 132 could alternatively be flush to the gripping surface 136 of the gripper arm 130 when unconstrained. Accordingly, the gripper lever 132 will be opened away from the gripper arm 130 when the rod 134 pulls the free end of the gripper lever 132. The leaflet 12 can then be grasped between the open gripper lever 132 and the open gripper arm 130. Releasing the rod 134 will therefore cause the gripper lever 132 to return to its unconstrained position, and hence grasp the leaflet 12 between itself and the gripper arm 130. The gripper lever 132 being biased to grasp the leaflet 12 when no forces are applied may result in a more secure and/or reliable hold of the leaflet 12.

Figure 24:
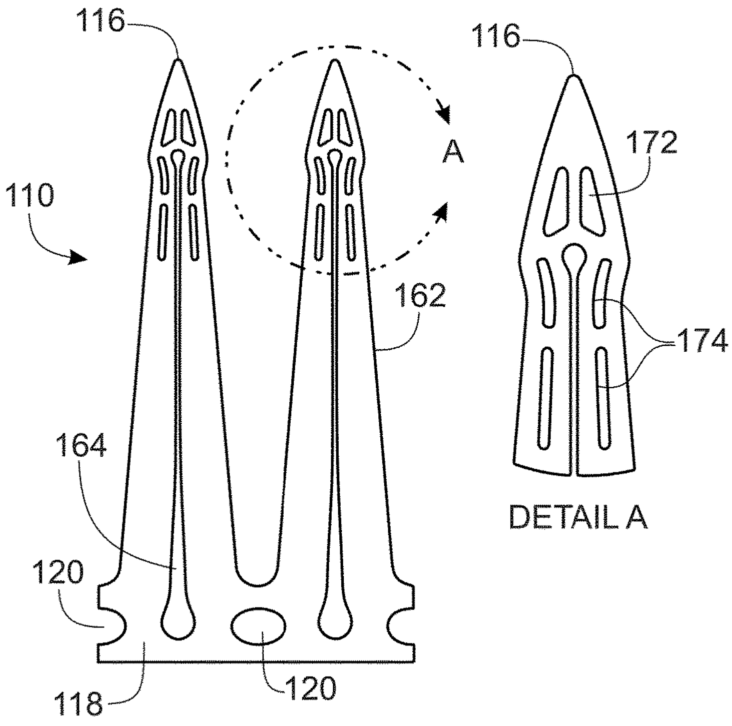
FIG. 24 shows a leaflet anchor in a two-dimensional projected view.

FIG. 24 illustrates a two-dimensional projection of the leaflet anchor 110, which is otherwise tubular. The leaflet anchor 110 comprises a base 118 from which two pins 162 extend. The base comprises two holes 120 for accommodating the artificial chordae line 114. The artificial chordae line 114 can be knotted to the leaflet anchor 110 using the holes 120. Extending along the length of the anchor pins 162 are two slits 164. The pins 162 extend in a straight direction when the leaflet anchor is in a folded configuration, and will return an unfolded configuration when unconstrained. The leaflet anchor 110 folds and unfolds similarly to the leaflet anchor 10 discussed above.

The tip 116 of the leaflet anchor 110 is shown in more detail in the close-up view of FIG. 24. The pins 162 of the leaflet anchor 110 flare towards the tip 116 of the anchor 110, before narrowing to a point at the tip 116. The tip 116 is pointed so that the leaflet anchor 110 can pierce the leaflet 12 during implantation. A number of apertures 172 and slits 174 are located along the pins 162 of the anchor 110, towards the tip 116 of the anchor. The apertures 172 and slits 174 increase a surface area of the leaflet anchor 110 towards the tip 116 of the leaflet anchor 110. This may help ensure a stable placement in the leaflet 12 during implantation. Whilst two apertures 172 and four slits 174 are shown in FIG. 24, the leaflet anchor 110 could comprise any combination of apertures 172 or slits 174 which increase the surface area of the leaflet anchor 110.

Figure 25:
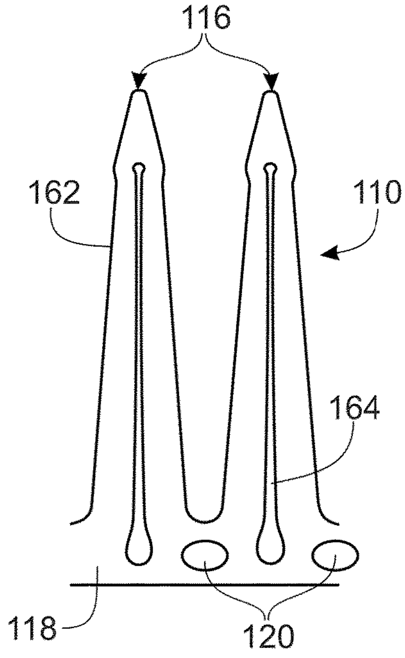
FIG. 25 shows an alternative leaflet anchor in a two-dimensional projected view.
Figure 26:
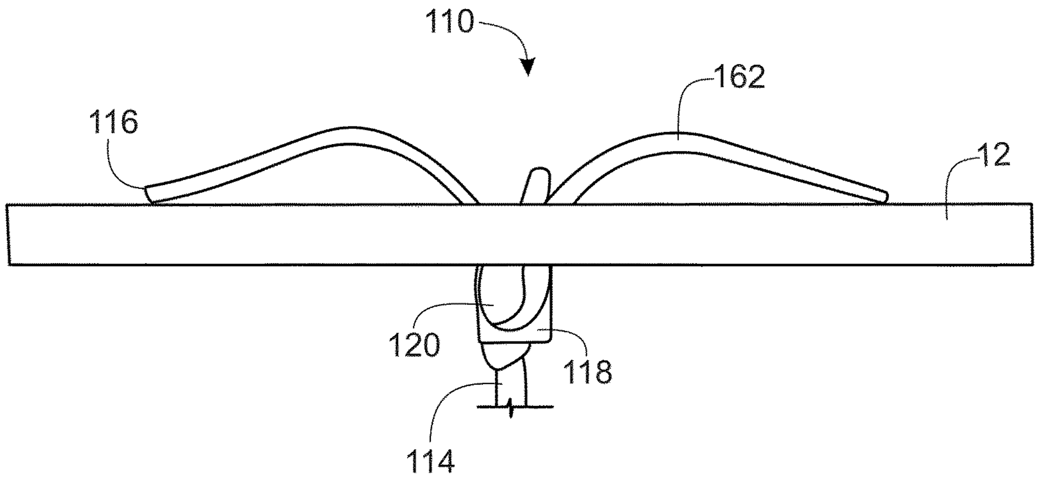
FIG. 26 shows a leaflet anchor implanted in a leaflet.

FIG. 25 shows another leaflet anchor 110. The tips 116 of the leaflet anchor 110 are rounded or dulled, such that the tips 116 are not as pointed or sharpened. By dulling the tips 116 of the pins 162 of the leaflet anchor 110, the leaflet anchor 110 may still be capable of piercing the leaflet 12, but the tips 116 may be less likely to pierce the leaflet 12 again once the leaflet anchor 110 has been implanted. It is desirous for the tips 116 of the leaflet anchor 110 to only pierce the leaflet 12 at the initial location of implantation, to avoid additional trauma to the leaflet 12. The tips may be dulled to a radius of between 0.1 mm to 1.0 mm. The tips may be dulled to a radius of 1 mm. Tolerances of ±2%, ±5% and ±8% may apply FIG. 26 illustrates the leaflet anchor 110 with dull tips 116 in combination with the artificial chordae line 114, implanted in the leaflet 12. The leaflet anchor 110 pierces the leaflet 12 at a first location, and as the pins 162 unfold during implantation, the tips 116 come to rest adjacent to the leaflet 12 at a second position. The dull tips 116 sit adjacent to the tissue of the leaflet 12, but due to being dulled rather than pointed, the pins 162 of the leaflet anchor 110 are less likely to pierce the leaflet 12 at the second location once the leaflet anchor 110 has been implanted. The pins 162 of the leaflet anchor 110 can therefore extend in a flatter, more elongate configuration relative to the surface of the leaflet 12. The contact area between the leaflet 12 and the pins 162 is therefore increases, and the leaflet anchor 110 is more secure in the leaflet 12 once implanted due to a better interference fit between the pins 162 and the leaflet 12.

Figure 27:
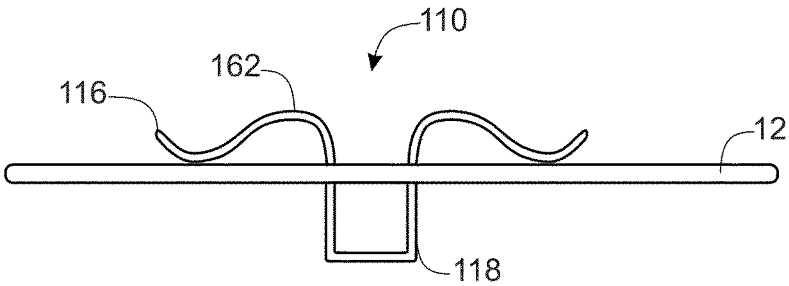
FIG. 27 shows an alternative leaflet anchor implanted in a leaflet.

Alternatively to the pins 162 of the leaflet anchor 110 extending in an elongate fashion adjacent to the leaflet 12, the pins 162 of the leaflet anchor 110 can be formed so that the tip 116 of the pins 162 is formed to point away from the leaflet 12. FIG. 27 shows the leaflet anchor 110 implanted in the leaflet 12. The base 118 of the leaflet anchor 110 remains on the side of the leaflet 12 from which the anchor 110 is initially implanted, and the pins 162 extend through the other side of the leaflet 12. The pins 162 unfold following implantation, and extend along a direction substantially parallel to the surface of the leaflet 12. To prevent the tips 116 of the pins 162 abrading or piercing the leaflet 12 at the second position, the pins 162 are formed such that the tips 116 will point or deflect away from the surface of the leaflet 12, in the unfolded position. This may be possible by using an elastic, memory metal material such as nitinol or stainless steel as discussed above.

Figure 28:
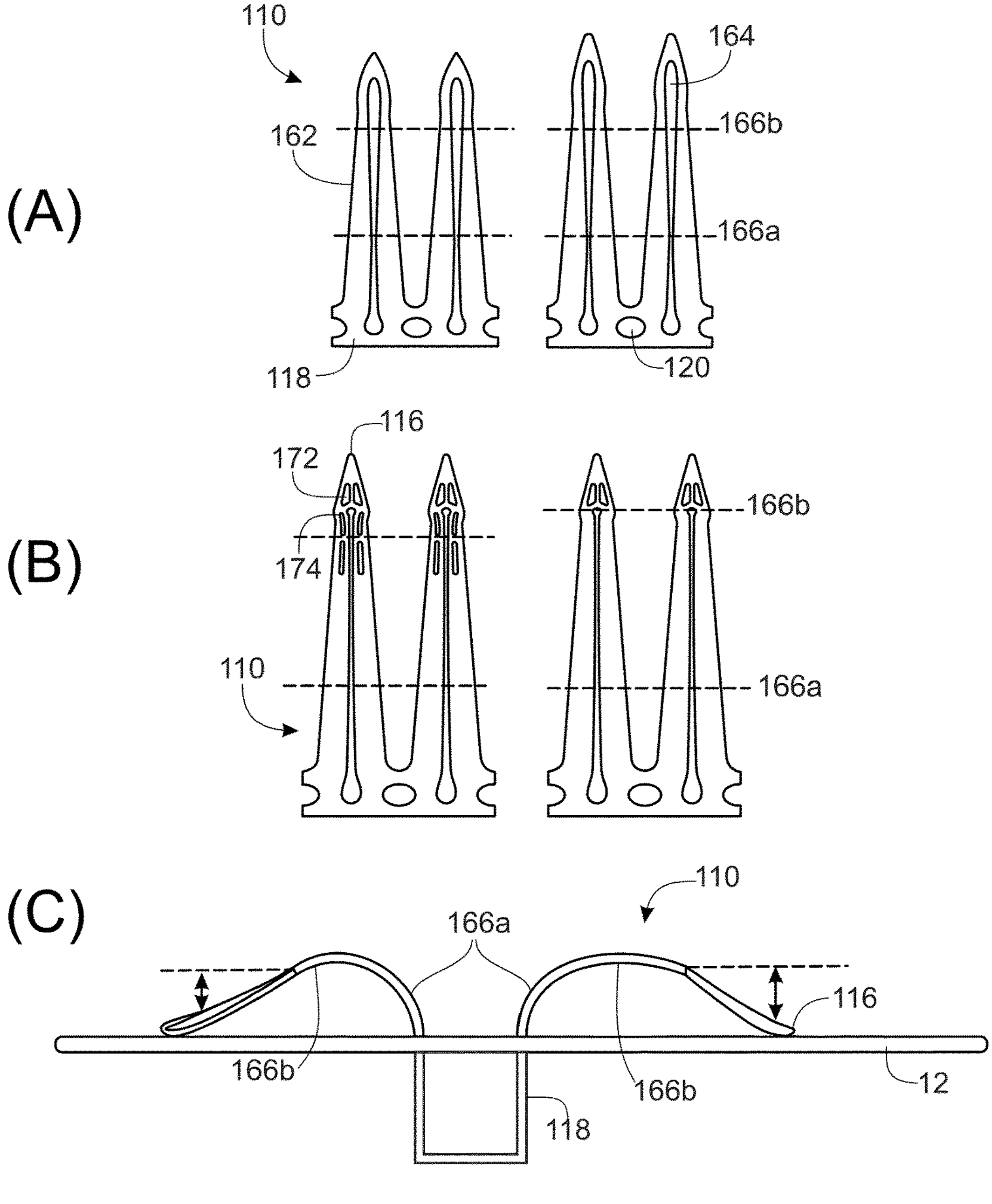
FIGS. 28A and 28B show alternative arrangements for the leaflet anchor.
FIG. 28C shows the leaflet anchor of either FIG. 28A or 28B implanted in the leaflet.

FIGS. 28A, 28B and 28C show an alternative arrangement for the leaflet anchor 110. The leaflet anchor 110 is formed with two hinge or deflection points 166*a*, 166*b* in the pins 162. The first deflection point 166*a* is located towards the base 118 of the leaflet anchor 110, whilst the second deflection point 166*b* is located towards the tip 116 of the pins 162.

FIG. 28C shows a cross-sectional view of the unfolded anchors 110 shown in FIGS. 28A and 28B. The leaflet anchor 110 is implanted in the leaflet 12, and the pins 162 are in the unfolded position. The pins 162 deflect at each of the deflection points 166*a*, 166*b*. The first deflection point 166*a* causes the pins 162 to extend back towards the surface of the leaflet 12, whilst the second deflection point 166*b* causes the pins 162 and their respective tips 116 go deflect away from the surface of the leaflet 12. The deflection points 166*a*, 166*b* define a point of inflection in the shape of the pins 162. The deflection points 166*a*, 166*b* soften the stiffness profile of the leaflet 12, and each carry additional benefits. The second deflection point 166*b* deflects the tips 116 of the pins 162 such that any abrasion of the leaflet 12 caused by the tips 116 can be reduced, when the implanted anchor 110 is moved during the cardiac cycle or otherwise. The first deflection point 166*a* increases a holding force of the leaflet anchor 110 when implanted in the leaflet 12, by biasing the pins 162 in a region adjacent to the location of implantation towards the surface of the leaflet 12. The first deflection point 166*a* may therefore act to 'pull' the base 118 of the leaflet anchor 110 towards surface of the leaflet 12 in which it is implanted.

Whilst multiple arrangements for the leaflet anchor 110 have been described in FIGS. 24 to 28C, many features of each arrangement may be combined in a single design of the leaflet anchor 110. Additionally, various aspects of the above-discussed leaflet anchors 110 can be implemented as desired, such that the design of the leaflet anchor 110 can be tailored based on the requirements of the procedure to be performed. Different anchor designs could be available for a surgeon to select based on their assessment of the patient.

Figure 29:
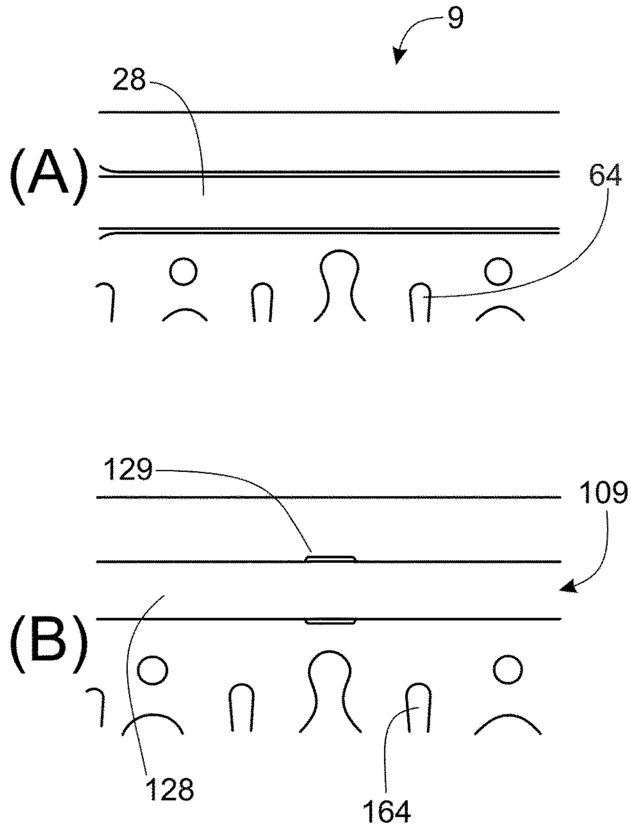
FIGS. 29A and 29B show two different arrangements for a locking segment of a papillary anchor.

FIG. 29A shows in closer detail the locking segment 28 of the papillary anchor 9, as also illustrated in FIG. 18. The locking segment 28 is located at the base of the papillary anchor 9, and comprises a band formed between two parallel slits. The locking segment 28 is arranged to hold the artificial chordae line 14, such that it is attached to the papillary anchor 9. The locking segment 28 is arranged such that the band will open when a force is applied, before returning to its closed position, flush with the surface of the base of the papillary anchor 9. The locking segment 28 can therefore open and close, which can facilitate adjustment of the artificial chordae line 14. The artificial chordae line 14 will be placed between the open band of the locking segment 28, and when the band closes the locking segment 28 will secure the artificial chordae line 14 when passed through the parallel slits.

FIG. 29B illustrates an alternative arrangement for a locking segment 128 of a papillary anchor 109. The overall structure of the papillary anchor 109 is similar to the papillary anchor 9 discussed above, and the papillary anchor 109 also includes central slits 164 along the hooks or pins 162 of the anchor 109. The parallel slits either side of the band of the locking segment 128 further include a respective opening 129. The opening 129 provides a gap between the band and the base of the papillary anchor 109, such that when the artificial chordae line 114 is secured to the papillary anchor 109 flattening or crimping of the artificial chordae line 114 can be reduced. It will be understood that the suture 114 will still be flattened or crimped by the locking segment 128 when secured, such that the artificial chordae line 114 is firmly held by the locking segment 128. Additionally, the provision of the openings 129 may help locate the artificial chordae line 114 at a consistent circumferential location of the locking segment 128.

Figure 30:
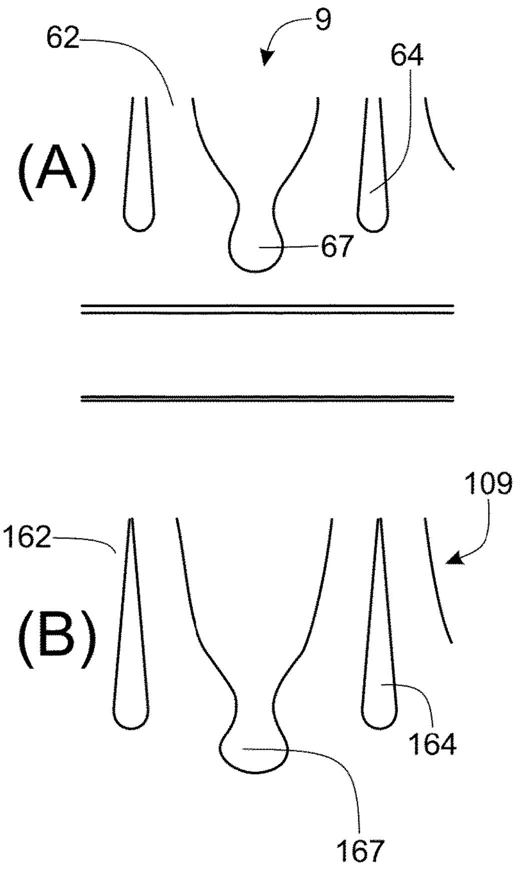
FIGS. 30A and 30B show two different arrangements for the shape of the base of the papillary anchor.

FIG. 30A shows in closer detail the base of the papillary anchor 9. The papillary anchor 9 includes a plurality of hooks or pins 62 extending from the base of the papillary anchor 9. Between adjacent pins is a keyhole 67. The keyhole 67 accommodates the free end of the artificial chordae line 14 when it is held in place by the locking segment 28.

FIG. 30B shows in closer detail an alternative arrangement for the base of the papillary anchor 109. The papillary anchor 109 includes a plurality of hooks or pins 162 extending from the base of the papillary anchor 109, and as such the overall structure of the papillary anchor 109 is similar to the papillary anchor 9 as discussed above. However, a keyhole 167 of the alternative papillary anchor 109 is widened such that it is ovoid in shape, rather than being circular. The widening of the keyhole 167 better accommodates the end of the artificial chordae line 114, which may have been flattened or crimped by the locking segment 128.

Whilst the locking segment openings 129 discussed in relation to FIG. 29B and the widened keyhole 167 of the papillary anchor 109 have been discussed separately, these features may also both be included in the same papillary anchor design.

Figure 31:
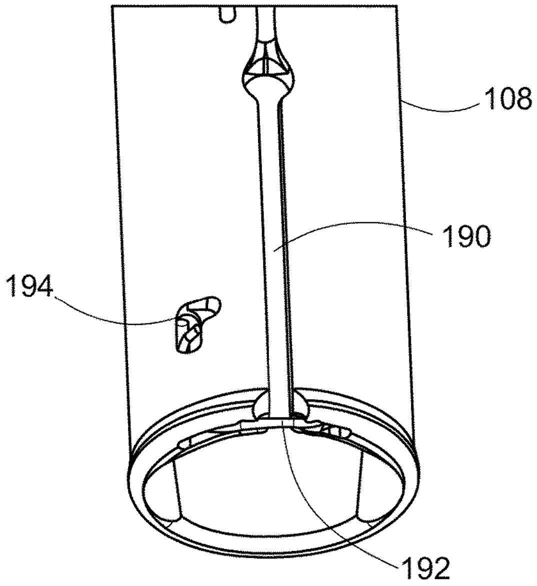
FIG. 31 shows a chordae locking device for the catheter device.

FIG. 31 illustrates the distal part 108 of the main body of the catheter device 102. The distal part 108 includes an opening at a distal end, from which the papillary anchor 109 will be deployed. The distal part 108 includes a channel 190 that holds the artificial chordae line 114, and allows the artificial chordae line 114 to be deployed from the catheter device 102 whilst attached simultaneously to the leaflet anchor 110 and the papillary anchor 109.

At a distal end of the channel 190 is a chordae lock 192. The chordae lock 192 is disposed across the channel 190. The chordae lock 192 prevents natural chordae tendineae from getting entangled in the distal part 108 of the catheter device 102 during a procedure. To achieve this, the chordae lock 192 is biased such that the chordae lock 192 will deflect in an outwards direction from the circumferential surface of the distal part 108. However, the chordae lock 192 will not open inwards. Thus, when the artificial chordae line 114 is to be deployed, a force can be exerted from within the distal part 108 to open the chordae lock 192. However, when the natural chordae tendineae are proximate to the channel 190, they will be prevented from entering the channel by the chordae lock 192. As such entanglement of the natural chordae tendineae with the catheter device 102 is prevented, avoiding any trauma or damage to the chordae tendineae.

The chordae lock 192 can be housed within a dedicated lock channel 194. The lock channel 194 can be formed within a wall of the distal part 108 of the main body of the catheter device 102, such that the chordae lock 192 does not extend beyond the axial or radial extend of the main body of the catheter device 102. The chordae lock 192 can extend in an axial direction within the channel 194, before extending at a right-angle or substantially perpendicular angle to extend across the channel 190. The chordae lock 192 can also include a further bend at a proximal end of the chordae lock 192 to prevent the chordae lock 192 from being pulled out of the lock channel 194.

The chordae lock 192 can comprise a heat-set nitinol wire, which at rest is in a closed position across the channel 190. The nitinol wire can be arranged to elastically deform under the application of a force to open the chordae lock 192, before returning to its initial position upon withdrawal of the force.

The invention claimed is:

1. A catheter device for repair of the heart by implanting an artificial chordae line, the catheter device comprising:
- a housing section extending from a distal end of the catheter device along the length of the catheter device toward a proximal end of the catheter device;
- a leaflet anchor for placement in a leaflet of a heart valve, wherein the leaflet anchor is arranged to be coupled to the artificial chordae line; and
- a leaflet anchor deployment mechanism for deploying the leaflet anchor to attach it to the leaflet of the heart, wherein the leaflet anchor deployment mechanism comprises a mechanical gripper device for grasping the leaflet of the heart valve, and a leaflet anchor tube for housing the leaflet anchor in a folded configuration;
- the mechanical gripper device and the leaflet anchor being arranged such that when, in use, the gripper device grasps the leaflet, the leaflet anchor can be pushed out of the leaflet anchor tube to pierce the leaflet and form the leaflet anchor into an unfolded configuration so that hooked formations of the leaflet anchor can, in use, secure the leaflet anchor in the leaflet;
- wherein the mechanical gripper device includes a gripper arm rotatably coupled to a main body of the catheter device so that the gripper arm can rotate relative to the catheter device to move an outer end of the gripper arm away from the main body of the catheter device;
- wherein the leaflet anchor tube is arranged to implant the leaflet anchor in the leaflet of the heart by piercing the leaflet from an atrial side of the leaflet;
- wherein the leaflet anchor tube is formed in the main body of the catheter device; and
- wherein an opening of the leaflet anchor tube is located on a surface of the main body of the catheter device, such that the leaflet anchor is deployed from the main body of the catheter device.

2. A catheter device as claimed in claim 1, wherein the leaflet anchor is arranged to be deployed by pushing it out of an opening at the end of the leaflet anchor tube, wherein the opening is arranged to be in contact with an atrial side of the leaflet of the heart during deployment.

3. A catheter device as claimed in claim 1, wherein the leaflet anchor is arranged to be pushed out of the leaflet anchor deployment mechanism from the proximal end of the catheter device toward the distal end of the catheter device.

4. A catheter device as claimed in claim 1, wherein the leaflet anchor is arranged to be deployed such that the artificial chordae line will be in contact with an atrial side of the leaflet of the heart between the leaflet anchor and an edge of the leaflet.

5. A catheter device as claimed in claim 1, wherein the gripper arm is shorter in length than the leaflet anchor when in the folded configuration.

6. A catheter device as claimed in claim 1, wherein the gripper arm is arranged to meet the opening of the leaflet anchor tube.

7. A catheter device as claimed in claim 1, wherein the gripper arm is configured to grasp the leaflet such that the leaflet anchor tube is arranged to implant the leaflet anchor toward an annulus of the leaflet.

8. A catheter as claimed in claim 1, comprising a hinge mechanism for the gripper arm, wherein the hinge mechanism is formed integrally with the material of the main body and rotates away from the main body by elastic deformation of that material.

9. A catheter as claimed in claim 8, wherein a single wire is provided to actuate the gripper arm by bending the hinge mechanism to rotate the end of the gripper arm away from the main body, with the gripper arm returning elastically to its rest position if no force is applied to the wire.

10. A catheter device as claimed in claim 1, wherein the housing section is a two-part housing section, the catheter device comprising:
- the two-part housing section extending from the distal end of the catheter device along the length of the catheter device toward the proximal end of the catheter device, the two-part housing section comprising a distal part at the distal end of the catheter device and a proximal part located on the proximal side of the distal part;
- the leaflet anchor deployment mechanism being at the proximal part of the housing section;
- a papillary anchor deployment mechanism at the distal part of the housing section for deployment of a papillary anchor for attachment to the papillary muscle, wherein the papillary anchor deployment mechanism is arranged for deployment of the papillary anchor by moving it outward in the distal direction relative to the distal part; and a flexible joint located between the proximal part and the distal part of the two-part housing section, wherein the flexible joint allows a centreline of the distal part to be angled relative to a centreline of the proximal part.

11. A catheter device as claimed in claim 10, wherein the gripper arm is provided in the proximal part of the two-part housing section and is rotatably coupled to the catheter device.

12. A catheter device as claimed in claim 1, wherein the leaflet anchor deployment mechanism allows for retraction and repositioning of the leaflet anchor after deployment of the anchor into the leaflet via an ejector unit having a grasping device with a first configuration arranged to permit deployment of the leaflet anchor into the leaflet without disengagement of the leaflet anchor from the ejector unit, and a second configuration in which the leaflet anchor is reversibly released from the ejector unit; wherein in the first configuration the grasping device of the ejector unit grasps a proximal end of the leaflet anchor, whilst a distal end of the leaflet anchor is unimpeded by the grasping device to enable it to be implanted in the leaflet; and wherein in the second configuration the grasping device of the ejector unit is disengaged from the leaflet anchor.

13. A catheter device as claimed in claim 1, comprising a linear-shaped rod for deployment of the leaflet anchor.

14. A catheter device as claimed in claim 1, wherein the opening of the leaflet anchor tube is located at a first position on the surface of the main body of the catheter device when the gripper arm is arranged in an open position, and wherein the opening of the leaflet anchor tube remains located at the first position when the gripper arm is in a closed position and arranged to meet the opening of the leaflet anchor tube.

15. A catheter device as claimed in claim 1, wherein the leaflet anchor tube is formed as a channel in the main body of the catheter device, and wherein the gripper arm includes one or more grooves, such that the leaflet anchor is deployed from the channel of the catheter device and configured to be recessed in the one or more grooves of the gripper arm.

16. A method of use of the catheter device of claim 1 for repair of the heart by implanting an artificial chordae line, the method comprising:

moving an outer end of the gripper arm away from the main body of the catheter device;

grasping the leaflet between the gripper arm and the main body of the catheter device by moving the outer end of the gripper arm back towards the main body of the catheter device; and pushing the leaflet anchor out of the leaflet anchor tube to pierce the leaflet from an atrial side and form the leaflet anchor into an unfolded configuration so that hooked formations of the leaflet anchor secure the leaflet anchor in the leaflet.

17. A method of manufacture of the catheter device as claimed in claim 1, the method comprising forming the main body of the catheter device from an elastic material.

* * * * *